(12) United States Patent
Nhan et al.

(10) Patent No.: US 8,450,555 B2
(45) Date of Patent: May 28, 2013

(54) STRETCHABLE ABSORBENT ARTICLE

(75) Inventors: Davis Dang Hoang Nhan, Appleton, WI (US); Mark M. Mleziva, Appleton, WI (US); Lawrence H. Sawyer, Neenah, WI (US); Peiguang Zhou, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 234 days.

(21) Appl. No.: 12/960,853

(22) Filed: Dec. 6, 2010

(65) Prior Publication Data

US 2011/0112498 A1    May 12, 2011

Related U.S. Application Data

(63) Continuation of application No. 10/699,193, filed on Oct. 31, 2003, now Pat. No. 7,872,168.

(51) Int. Cl.
*A61F 13/15* (2006.01)
*A61F 13/20* (2006.01)

(52) U.S. Cl.
USPC .......................................... 604/367; 604/382

(58) Field of Classification Search
USPC .................................................. 604/367, 368
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,761,348 A | 9/1973 | Chamberlin | |
| 3,802,817 A | 4/1974 | Matsuki et al. | |
| 3,839,240 A | 10/1974 | Zimmerman | |
| 3,849,241 A | 11/1974 | Butin et al. | |
| 3,901,236 A | 8/1975 | Assarsson et al. | |
| 4,050,462 A | 9/1977 | Woon et al. | |
| 4,076,663 A | 2/1978 | Masuda et al. | |
| 4,100,324 A | 7/1978 | Anderson et al. | |

(Continued)

FOREIGN PATENT DOCUMENTS

| EP | 0217032 A2 | 4/1987 |
|---|---|---|
| EP | 0419742 A1 | 4/1991 |

(Continued)

OTHER PUBLICATIONS

International Search Report and Written Opinion for PCT/US2004/013184, dated Sep. 21, 2004; 5 pages.

*Primary Examiner* — Melanie Hand
(74) *Attorney, Agent, or Firm* — Armstrong Teasdale LLP

(57) ABSTRACT

An absorbent article having a stretchable substrate and an absorbent composite comprising a layer of adhesive composition in contact with the stretchable substrate. A layer of particulate superabsorbent material is applied to and held by the adhesive composition. The absorbent composite is secured to the substrate by the adhesive composition. The stretchable substrate has a recovery in at least one of the lateral direction and the longitudinal directions of the article as determined by an Elongation and Recovery Test, and the absorbent article has a recovery in the at least one of the lateral direction and the longitudinal direction as determined by the Elongation and Recovery Test that is at least about 60 percent of the recovery of the substrate in the at least one of the lateral direction and the longitudinal direction.

23 Claims, 13 Drawing Sheets

U.S. PATENT DOCUMENTS

| | | | |
|---|---|---|---|
| 4,138,459 A | 2/1979 | Brazinsky et al. |
| 4,286,082 A | 8/1981 | Tsubakimoto et al. |
| 4,340,563 A | 7/1982 | Appel et al. |
| 4,384,023 A | 5/1983 | Okamura et al. |
| 4,573,986 A | 3/1986 | Minetola et al. |
| 4,590,124 A | 5/1986 | Schoenberg |
| 4,613,643 A | 9/1986 | Nakamura et al. |
| 4,663,220 A | 5/1987 | Wisneski et al. |
| 4,675,209 A | 6/1987 | Pedigrew |
| 4,698,372 A | 10/1987 | Moss |
| 4,704,114 A | 11/1987 | Wilson et al. |
| 4,704,116 A | 11/1987 | Enloe |
| 4,710,187 A | 12/1987 | Boland et al. |
| 4,720,415 A | 1/1988 | Vander Wielen et al. |
| 4,724,114 A | 2/1988 | McFarland et al. |
| 4,752,349 A | 6/1988 | Gebel |
| 4,820,590 A | 4/1989 | Hodgson, Jr. et al. |
| 4,833,172 A | 5/1989 | Schwarz et al. |
| 4,865,597 A | 9/1989 | Mason, Jr. et al. |
| 4,874,451 A | 10/1989 | Boger et al. |
| 4,879,170 A | 11/1989 | Radwanski et al. |
| 4,940,464 A | 7/1990 | Van Gompel et al. |
| 4,992,324 A | 2/1991 | Dube |
| 4,994,335 A | 2/1991 | Kamaei et al. |
| 5,002,814 A | 3/1991 | Knack et al. |
| 5,046,272 A | 9/1991 | Vogt et al. |
| 5,073,316 A | 12/1991 | Bizen et al. |
| 5,104,116 A | 4/1992 | Pohjola |
| 5,153,254 A | 10/1992 | Chen |
| 5,169,712 A | 12/1992 | Tapp |
| 5,213,881 A | 5/1993 | Timmons et al. |
| 5,224,405 A | 7/1993 | Pohjola |
| 5,226,992 A | 7/1993 | Morman |
| 5,304,599 A | 4/1994 | Himes |
| 5,332,613 A | 7/1994 | Taylor et al. |
| 5,340,424 A | 8/1994 | Matsushita |
| 5,364,382 A | 11/1994 | Latimer et al. |
| 5,382,400 A | 1/1995 | Pike et al. |
| 5,385,775 A | 1/1995 | Wright |
| 5,397,317 A | 3/1995 | Thomas |
| 5,405,887 A | 4/1995 | Morita et al. |
| 5,486,166 A | 1/1996 | Bishop et al. |
| 5,490,846 A | 2/1996 | Ellis et al. |
| 5,496,429 A | 3/1996 | Hasse et al. |
| 5,503,076 A | 4/1996 | Yeo |
| 5,503,908 A | 4/1996 | Faass |
| 5,536,264 A | 7/1996 | Hsueh |
| 5,560,878 A | 10/1996 | Dragoo et al. |
| 5,615,460 A | 4/1997 | Weirich et al. |
| 5,634,916 A | 6/1997 | Lavon et al. |
| 5,643,242 A | 7/1997 | Lavon et al. |
| 5,695,376 A | 12/1997 | Datta et al. |
| 5,695,377 A | 12/1997 | Triebes et al. |
| 5,718,913 A | 2/1998 | Dhuique-Mayer et al. |
| 5,759,926 A | 6/1998 | Pike et al. |
| 5,763,331 A | 6/1998 | Demhartner |
| 5,766,389 A | 6/1998 | Brandon et al. |
| 5,789,065 A | 8/1998 | Haffner et al. |
| 5,800,419 A | 9/1998 | Soga et al. |
| 5,804,286 A | 9/1998 | Quantrille et al. |
| 5,814,390 A | 9/1998 | Stokes et al. |
| 5,853,638 A | 12/1998 | Han |
| 5,853,881 A | 12/1998 | Estey et al. |
| 5,858,292 A | 1/1999 | Dragoo et al. |
| 5,879,751 A | 3/1999 | Bogdanski |
| 5,885,908 A | 3/1999 | Jaeger et al. |
| 5,981,689 A | 11/1999 | Mitchell et al. |
| 6,057,024 A | 5/2000 | Mleziva et al. |
| 6,072,101 A | 6/2000 | Beihoffer et al. |
| 6,080,909 A | 6/2000 | Osterdahl et al. |
| 6,087,448 A | 7/2000 | Mitchell et al. |
| 6,096,014 A | 8/2000 | Haffner et al. |
| 6,103,358 A | 8/2000 | Bruggemann et al. |
| 6,103,953 A | 8/2000 | Cree et al. |
| 6,121,409 A | 9/2000 | Mitchell et al. |
| 6,150,002 A | 11/2000 | Varona |
| 6,159,591 A | 12/2000 | Beihoffer et al. |
| 6,160,197 A | 12/2000 | Lassen et al. |
| 6,187,425 B1 | 2/2001 | Bell et al. |
| 6,194,631 B1 | 2/2001 | Mitchell et al. |
| 6,200,669 B1 | 3/2001 | Marmon et al. |
| 6,221,062 B1 | 4/2001 | Osborn, III |
| 6,222,091 B1 | 4/2001 | Beihoffer et al. |
| 6,235,965 B1 | 5/2001 | Beihoffer et al. |
| 6,290,686 B1 | 9/2001 | Tanzer |
| 6,319,342 B1 | 11/2001 | Riddell |
| 6,342,298 B1 | 1/2002 | Evans et al. |
| 6,376,072 B1 | 4/2002 | Evans et al. |
| 6,392,116 B1 | 5/2002 | Beihoffer et al. |
| 6,403,857 B1 | 6/2002 | Gross et al. |
| 6,417,120 B1 | 7/2002 | Mitchler et al. |
| 6,417,121 B1 | 7/2002 | Newkirk et al. |
| 6,417,122 B1 | 7/2002 | Newkirk et al. |
| 6,417,425 B1 | 7/2002 | Whitmore et al. |
| 6,420,285 B1 | 7/2002 | Newkirk et al. |
| 6,454,750 B1 | 9/2002 | Vogt et al. |
| 6,465,073 B1 | 10/2002 | Morman et al. |
| 6,503,855 B1 | 1/2003 | Menzies et al. |
| 6,506,698 B1 | 1/2003 | Quantrille et al. |
| 6,509,512 B1 | 1/2003 | Beihoffer et al. |
| 6,518,208 B2 | 2/2003 | Terakawa |
| 6,521,811 B1 | 2/2003 | Lassen et al. |
| 6,555,502 B1 | 4/2003 | Beihoffer et al. |
| 6,575,952 B2 | 6/2003 | Kirk et al. |
| 6,582,414 B1 | 6/2003 | Richardson |
| 6,585,713 B1 | 7/2003 | LeMahieu et al. |
| 6,586,354 B1 | 7/2003 | Topolkaraev et al. |
| 6,586,512 B1 | 7/2003 | Dukes et al. |
| 6,610,900 B1 | 8/2003 | Tanzer |
| 6,682,512 B2 | 1/2004 | Uitenbroek et al. |
| 7,795,336 B2 * | 9/2010 | Paul et al. ............ 524/277 |
| 2001/0001312 A1 | 5/2001 | Mitchell et al. |
| 2001/0007064 A1 | 7/2001 | Mitchell et al. |
| 2001/0029358 A1 | 10/2001 | Beihoffer et al. |
| 2001/0044612 A1 | 11/2001 | Beihoffer et al. |
| 2002/0007166 A1 | 1/2002 | Mitchell et al. |
| 2002/0013563 A1 | 1/2002 | Lassen et al. |
| 2002/0015846 A1 | 2/2002 | Evans et al. |
| 2002/0029029 A1 | 3/2002 | Otsubo |
| 2002/0068494 A1 | 6/2002 | Jackson et al. |
| 2002/0095127 A1 | 7/2002 | Fish et al. |
| 2002/0115969 A1 | 8/2002 | Maeda et al. |
| 2002/0120244 A1 | 8/2002 | Sawyer et al. |
| 2002/0169428 A1 | 11/2002 | Fell et al. |
| 2002/0193724 A1 | 12/2002 | Stebbings et al. |
| 2003/0014027 A1 | 1/2003 | Beihoffer et al. |
| 2003/0044562 A1 | 3/2003 | Li et al. |
| 2003/0088230 A1 | 5/2003 | Balogh et al. |
| 2003/0111163 A1 | 6/2003 | Ko et al. |
| 2003/0129915 A1 | 7/2003 | Harriz |
| 2004/0116014 A1 | 6/2004 | Soerens et al. |
| 2004/0127614 A1 | 7/2004 | Jiang et al. |

FOREIGN PATENT DOCUMENTS

| | | | |
|---|---|---|---|
| EP | 0432755 A1 | 6/1991 |
| EP | 0452727 A1 | 10/1991 |
| EP | 0497072 A1 | 8/1992 |
| EP | 0602613 A1 | 6/1994 |
| EP | 0676496 A2 | 10/1995 |
| EP | 0700672 A1 | 3/1996 |
| EP | 0700673 A1 | 3/1996 |
| EP | 0800808 A1 | 10/1997 |
| EP | 0880956 A2 | 2/1998 |
| FR | 2838445 A1 | 10/2003 |
| GB | 2103537 A | 2/1983 |
| GB | 2115702 A | 9/1983 |
| JP | 62-078214 A | 4/1987 |
| JP | 02007955 | 1/1990 |
| JP | 05331775 | 12/1993 |
| JP | 09-241961 A | 9/1997 |
| JP | 09253129 | 9/1997 |
| JP | 10075978 | 3/1998 |
| JP | 2001158074 | 6/2001 |
| WO | 94/00292 A1 | 1/1994 |
| WO | 95/15410 A1 | 6/1995 |
| WO | 96/01094 A1 | 1/1996 |
| WO | 96/09023 A1 | 3/1996 |

| | | | | | | |
|---|---|---|---|---|---|---|
| WO | 96/67380 | A1 | 3/1996 | WO | 01/87213 A1 | 11/2001 |
| WO | 98/02610 | A1 | 1/1998 | WO | 01/87214 A1 | 11/2001 |
| WO | 98/23305 | A1 | 6/1998 | WO | 01/87588 A2 | 11/2001 |
| WO | 98/29481 | A1 | 7/1998 | WO | 01/88245 A2 | 11/2001 |
| WO | 98/29504 | A1 | 7/1998 | WO | 02/10032 A2 | 2/2002 |
| WO | 99/25393 | A2 | 5/1999 | WO | 02/053364 A2 | 7/2002 |
| WO | 99/25745 | A1 | 5/1999 | WO | 03/018671 A1 | 3/2003 |
| WO | 99/25748 | A1 | 5/1999 | WO | 03/037392 A1 | 5/2003 |
| WO | 00/37009 | A2 | 6/2000 | WO | 03/049662 A1 | 6/2003 |
| WO | 00/56959 | A1 | 9/2000 | WO | 03/057119 A2 | 7/2003 |
| WO | 00/63295 | A1 | 10/2000 | WO | 03/057121 A1 | 7/2003 |
| WO | 01/00053 | A1 | 1/2001 | WO | 03/059228 A2 | 7/2003 |
| WO | 01/05440 | A2 | 1/2001 | | | |
| WO | 01/23177 | A1 | 4/2001 | | | |
| WO | 01/87212 | A1 | 11/2001 | | | |

* cited by examiner

FIG. 11

| | | Load Value (grams-force) | | | | Normalized Load Value at 40% Elongation (grams-force) | Set % | | Recovery % | | Recovery Ratio Sample/ Substrate (%) |
|---|---|---|---|---|---|---|---|---|---|---|---|
| | | At 40% Elongation | | At 100% Elongation | | | | | | | |
| | Cycle | Sample | Substrate | Sample | Substrate | | Sample | Substrate | Sample | Substrate | |
| Lateral Direction | 1 | 473.1 | 343.4 | 833.1 | 693.8 | 157.7 | 45.9 | 43.7 | 54.1 | 56.3 | 96.1 |
| | 2 | 120.3 | 106.5 | 762.3 | 675.3 | 40.1 | 49.1 | 46.9 | 50.9 | 53.1 | 95.9 |
| | 3 | 80.2 | 73.1 | 735.9 | 663.1 | 26.7 | 49.1 | 46.9 | 50.9 | 53.1 | 95.9 |
| Longitudinal Direction | 1 | 1734.1 | 1473.9 | 2591.5 | 2206.3 | 578 | 33.7 | 32.2 | 66.3 | 67.8 | 97.8 |
| | 2 | 693.8 | 644.6 | 2489.8 | 2171.5 | 231.3 | 37 | 35.9 | 63.1 | 64.1 | 98.4 |
| | 3 | 552.7 | 511.6 | 2439.3 | 2141.6 | 184.23 | 37 | 35.9 | 63 | 64.1 | 98.3 |

FIG. 12

| | | Load Value (grams force) | | | | Normalized Load Value at 40% Elongation (grams-force) | Set % | | Recovery % | | Recovery Ratio Sample/Substrate (%) |
|---|---|---|---|---|---|---|---|---|---|---|---|
| | | At 40% Elongation | | At 100% Elongation | | | | | | | |
| | Cycle | Sample | Substrate | Sample | Substrate | | Sample | Substrate | Sample | Substrate | |
| Lateral Direction | 1 | 647.5 | 875 | 1251.9 | 1367.5 | 215.8 | 51.8 | 49.4 | 48.2 | 50.6 | 95.3 |
| | 2 | 39.7 | 44.3 | 1161.8 | 1362.7 | 13.2 | 55.2 | 52.9 | 44.8 | 47.1 | 95.1 |
| | 3 | 10.5 | 11.25 | 1111.9 | 1316.5 | 3.5 | 55.2 | 52.9 | 44.8 | 47.1 | 95.1 |
| Longitudinal Direction | 1 | 2512.2 | 2032.6 | 3472.3 | 2805.2 | 837.4 | 46.2 | 47 | 53.8 | 53 | 101.5 |
| | 2 | 189.3 | 116.1 | 3282.5 | 2724.3 | 63.1 | 50.1 | 50.7 | 49.9 | 49.3 | 101.2 |
| | 3 | 51.8 | 24.83 | 3167.2 | 2623.8 | 17.3 | 50.1 | 50.6 | 49.9 | 49.4 | 101 |

FIG. 13

| | | Load Value (grams force) | | | | Normalized Load Value at 40% Elongation (grams-force) | Set % | | Recovery % | | Recovery Ratio Sample/ Substrate (%) |
|---|---|---|---|---|---|---|---|---|---|---|---|
| | | At 40% Elongation | | At 100% Elongation | | | | | | | |
| | Cycle | Sample | Substrate | Sample | Substrate | | Sample | Substrate | Sample | Substrate | |
| Lateral Direction | 1 | 258.8 | 185.1 | 425.6 | 372.6 | 86.3 | 53.4 | 56.9 | 46.6 | 43.1 | 108.1 |
| | 2 | 41.3 | 21.6 | 404 | 366.5 | 13.8 | 57.2 | 60.3 | 42.8 | 39.7 | 107.8 |
| | 3 | 20.1 | 8.2 | 394 | 360.4 | 6.7 | 57.2 | 60.3 | 42.8 | 39.7 | 107.8 |
| Longitudinal Direction | 1 | 1501.8 | 1519 | 1774 | 1812.4 | 192.7 | 39.9 | 38.9 | 60.1 | 61.1 | 98.4 |
| | 2 | 547.5 | 476.1 | 1778.2 | 1839.5 | 182.5 | 44 | 42.8 | 56 | 57.2 | 97.9 |
| | 3 | 371 | 297.7 | 1766.7 | 1826.7 | 123.7 | 44 | 42.8 | 56 | 57.2 | 97.9 |

STRETCHABLE ABSORBENT ARTICLE

CROSS REFERENCE TO RELATED APPLICATION

This application is a continuation application of U.S. patent application Ser. No. 10/699,193, filed Oct. 31, 2003, which is hereby incorporated by reference in its entirety.

BACKGROUND OF THE INVENTION

The present invention relates generally to absorbent articles intended for personal wear, and more particularly to such absorbent articles having an absorbent composite secured to a stretchable substrate of the article.

Absorbent articles such as diapers, training pants, incontinence garments, feminine hygiene products, etc. conventionally comprise a liquid permeable body-facing liner, a liquid impermeable outer cover, and an absorbent core (also referred to as an absorbent body or absorbent structure) formed separate from the outer cover and liner and disposed therebetween for taking in and retaining liquid (e.g., urine, menses) exuded by the wearer. In some of these absorbent articles, the outer cover and/or the liner are stretchable to permit some expansion of the article when necessary to provide a better fit on the wearer. During use, the article is subjected to forces such as those generated by loading of the absorbent article and movement of the wearer. These forces can cause the absorbent core to shift within the absorbent article, to tear, or to otherwise become permanently distorted, all of which reduce the intended absorbent characteristics of the absorbent core and increase the possibility of liquid body exudates leaking from the article.

To this end, it is known to secure the separately formed absorbent structure to the outer cover and/or the liner, such as using adhesive or by thermal or ultrasonic bonding, to prevent the absorbent core from shifting as the article is stretched and unstretched during usage. However, securing the absorbent core to the outer cover or liner in this manner tends to reduce the stretchability of the substrate to which the absorbent core is secured, thereby reducing the flexibility of the absorbent article. Moreover, while securing the absorbent core to the outer cover and/or liner reduces the risk of shifting and distortion, stretching of the substrate to which the separately formed absorbent core is secured can still result in tearing of the absorbent core.

Also, conventional absorbent cores are typically constructed of superabsorbent material particles and hydrophilic fibers loosely mixed and entangled together to form an absorbent batt. In some absorbent cores, the superabsorbent material is concentrated in certain target areas of the absorbent article where more absorption is needed. When such an absorbent core is disposed between a stretchable outer cover and liner, the superabsorbent particles and hydrophilic fibers shift around as the absorbent article is stretched and unstretched during usage. The displacement of the superabsorbent particles and hydrophilic fibers from the target areas can lead to leakage from the absorbent article and/or, where the superabsorbent particles accumulate in a certain area, swelling of the particles upon absorbing liquid can make wearing the article feel uncomfortable. Such shifting may also lead to a degraded appearance and a perception of poor quality.

SUMMARY OF THE INVENTION

In general, an absorbent article according to one embodiment of the present invention comprises a stretchable substrate and an absorbent composite comprising a layer of adhesive composition in contact with the stretchable substrate. A layer of particulate superabsorbent material is applied to and held by the adhesive composition. The absorbent composite is secured to the substrate by the adhesive composition.

In another embodiment, the absorbent article generally comprises a stretchable substrate and an absorbent composite secured to the stretchable substrate. The absorbent composite comprises an adhesive composition and particulate superabsorbent material wherein the particulate superabsorbent material is held by the adhesive composition. The absorbent composite is secured to the substrate by the adhesive composition. The absorbent article has a longitudinal direction and a lateral direction. The stretchable substrate of the article has a recovery in at least one of the lateral direction and the longitudinal directions of the article as determined by an Elongation and Recovery Test, and the absorbent article has a recovery in the at least one of the lateral direction and the longitudinal direction as determined by the Elongation and Recovery Test that is at least about 60 percent of the recovery of the substrate in the at least one of the lateral direction and the longitudinal direction.

An absorbent composite according to one embodiment of the present invention generally comprises an adhesive composition and particulate superabsorbent material held by the adhesive composition. The adhesive composition has a viscosity of less than about 10,000 centipoises at a temperature of less than or equal to about 400 degrees Fahrenheit (about 204 degrees Celsius) and a storage modulus (G') of less than or equal to about $1.0 \times 10^7$ dyne/cm$^2$ at 25 degrees Celsius.

In one embodiment, a method of the present invention for making an absorbent article of which at least a portion is stretchable during use generally comprises applying a layer of adhesive composition to a stretchable substrate and applying a layer of particulate superabsorbent material to the adhesive composition after applying the adhesive composition to the stretchable substrate.

In another embodiment, the method generally comprises forming a mixture of adhesive composition and superabsorbent material, and then applying the mixture to a stretchable substrate whereby the adhesive composition holds the superabsorbent material on the substrate.

Other features of the invention will be in part apparent and in part pointed out hereinafter.

BRIEF DESCRIPTION OF THE DRAWINGS

FIG. 11 is a data table;

FIG. 12 is a second data table; and

FIG. 13 is a third data table.

Corresponding reference characters indicate corresponding parts throughout the several views of the drawings.

DEFINITIONS

Figure 1:
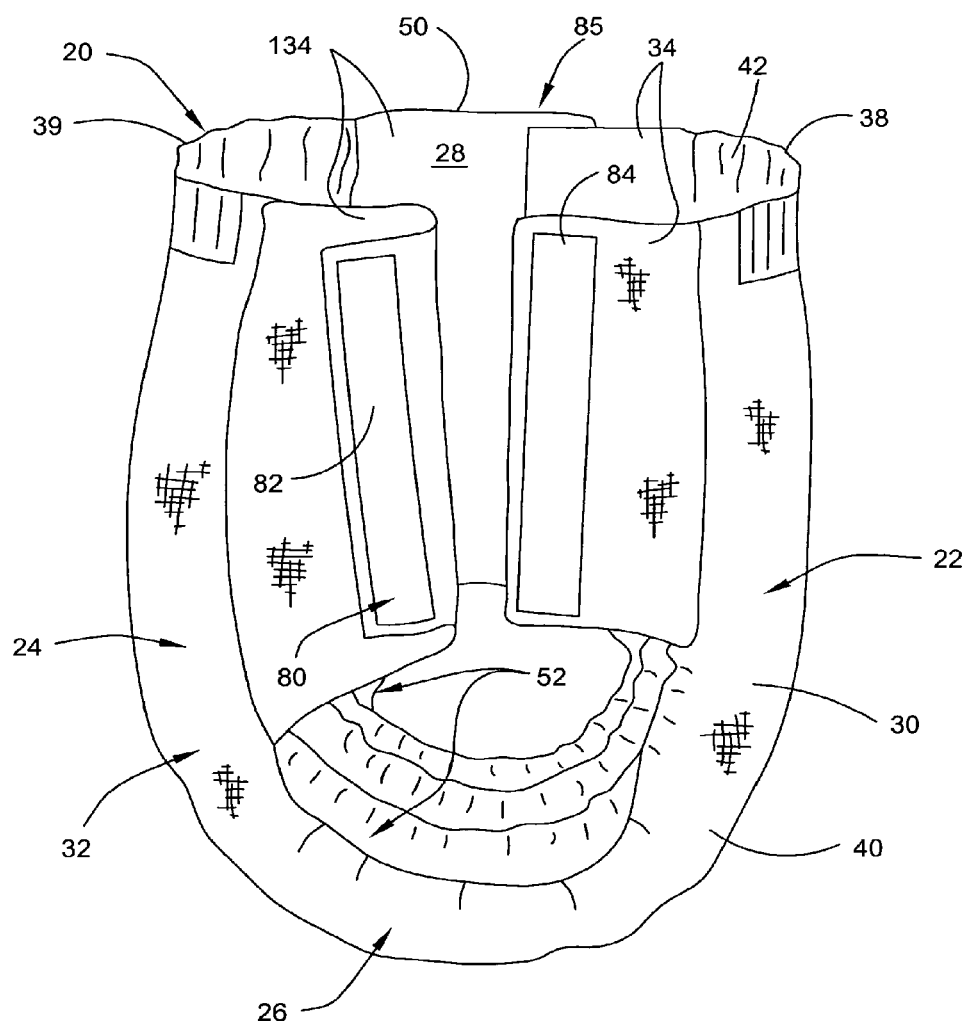
FIG. 1 is a side perspective of one embodiment of an absorbent article of the present invention shown in the form of a pair of training pants having a mechanical fastening system fastened on one side of the training pants and unfastened on the opposite side thereof.

Within the context of this specification, each term or phrase below includes the following meaning or meanings:

"Attached" refers to the joining, adhering, connecting, bonding, or the like, of two elements. Two elements will be considered to be attached to one another when they are attached directly to one another or indirectly to one another, such as when each is directly attached to intermediate elements.

"Hydrophilic" describes fibers or the surfaces of fibers and other materials which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "non-wettable" or hydrophobic.

"Layer" when used in the singular can have the dual meaning of a single element or a plurality of elements.

"Liquid impermeable," when used in describing a layer or multi-layer laminate means that liquid body waste, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al.

Meltblowing processes can be used to make fibers of various dimensions, including macrofibers (with average diameters from about 40 to about 100 microns), textile-type fibers (with average diameters between about 10 and 40 microns), and microfibers (with average diameters less than about 10 microns). Meltblowing processes are particularly suited to making microfibers, including ultra-fine microfibers (with an average diameter of about 3 microns or less). A description of an exemplary process of making ultra-fine microfibers may be found in, for example, U.S. Pat. No. 5,213,881 to Timmons, et al.

Meltblown fibers may be continuous or discontinuous and are generally self bonding when deposited onto a collecting surface. Meltblown fibers used in the present invention are suitably substantially continuous in length.

"Non-woven" as used in reference to a material, web or fabric refers to such a material, web or fabric having a structure of individual fibers or threads that are interlaid, but not in a regular or identifiable manner as in a knitted fabric. Non-woven materials, fabrics or webs have been formed from many processes such as, for example, meltblowing processes, spunbonding processes, air laying processes, and bonded carded web processes. The basis weight of non-wovens is usually expressed in ounces of material per square yard (osy) or grams per square meter (gsm) and the fiber diameters are usually expressed in microns. (Note: to convert from osy to gsm, multiply osy by 33.91.).

"Spunbonded fibers", or "spunbond fibers", means small-diameter fibers that are typically formed by extruding molten thermoplastic material as filaments from a plurality of fine capillaries of a spinneret having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al., each of which is incorporated by reference in its entirety and in a manner consistent with the present document. Spunbond fibers are quenched and generally not tacky when they are deposited onto a collecting surface. Spunbond fibers are generally continuous and often have average diameters larger than about 7 microns, and more particularly between about 10 and 30 microns. A spunbond material, layer, or substrate comprises spunbonded (or spunbond) fibers.

"Thermoplastic" describes a material which softens when exposed to heat and which substantially returns to a non-softened condition when cooled to room temperature.

DETAILED DESCRIPTION OF THE PREFERRED EMBODIMENTS

Referring now to the drawings and in particular to FIG. 1, one embodiment of an absorbent article of the present invention is illustrated in the form of children's toilet training pants and is indicated in its entirety by the reference numeral 20. The absorbent article 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing training pants such as the pants 20 of FIG. 1 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat.

No. 5,766,389 issued Jun. 16, 1998 to Brandon et al., which are incorporated herein by reference.

The pair of training pants 20 is illustrated in FIG. 1 in a partially fastened condition and comprises longitudinal end regions, further referred to herein as a front waist region 22 and a back waist region 24, and a center region, further referred to herein as a crotch region 26, extending longitudinally between and interconnecting the front and back waist regions. The pants 20 has an inner surface 28 which faces the wearer and an outer surface 30 which faces away from the wearer. The front and back waist regions 22, 24 comprise those portions of the pants 20 which, during wear, wholly or partially cover or encircle the waist or mid-lower torso of the wearer. The crotch region 26 generally comprises that portion of the pants 20 which, during wear, is positioned between the legs of the wearer and covers the lower torso and crotch of the wearer. With additional reference to FIGS. 2 and 3, the pair of training pants 20 has laterally opposite side edges 36 and longitudinally opposite waist edges, respectively designated front waist edge 38 and back waist edge 39.

The illustrated pants 20 comprises a central absorbent assembly, generally indicated at 32, a pair of laterally opposite front side panels 34 extending outward therefrom at the front waist region 22 and a pair of laterally opposite back side panels 134 extending outward therefrom at the back waist region 24. The central absorbent assembly 32 of the illustrated embodiment is generally rectangular. However, it is contemplated that the central absorbent assembly 32 may be other than rectangular, such as hourglass shaped, T-shaped, I-shaped, and the like without departing from the scope of this invention.

Figure 2:
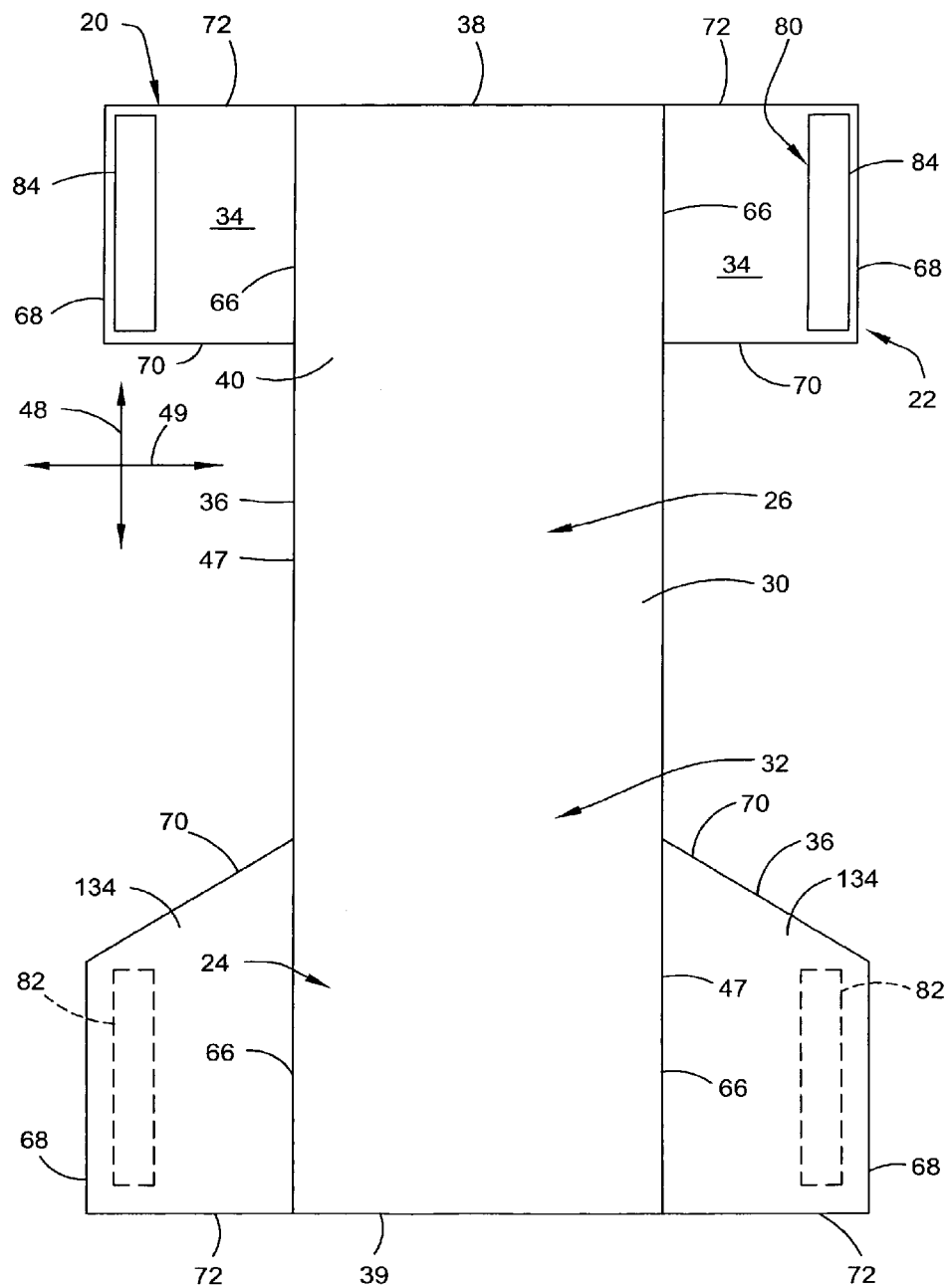
FIG. 2 is a bottom plan view of the training pants of FIG. 1 with the pants shown in an unfastened, unfolded and laid flat condition, and showing the surface of the training pants that faces away from the wearer.
Figure 3:
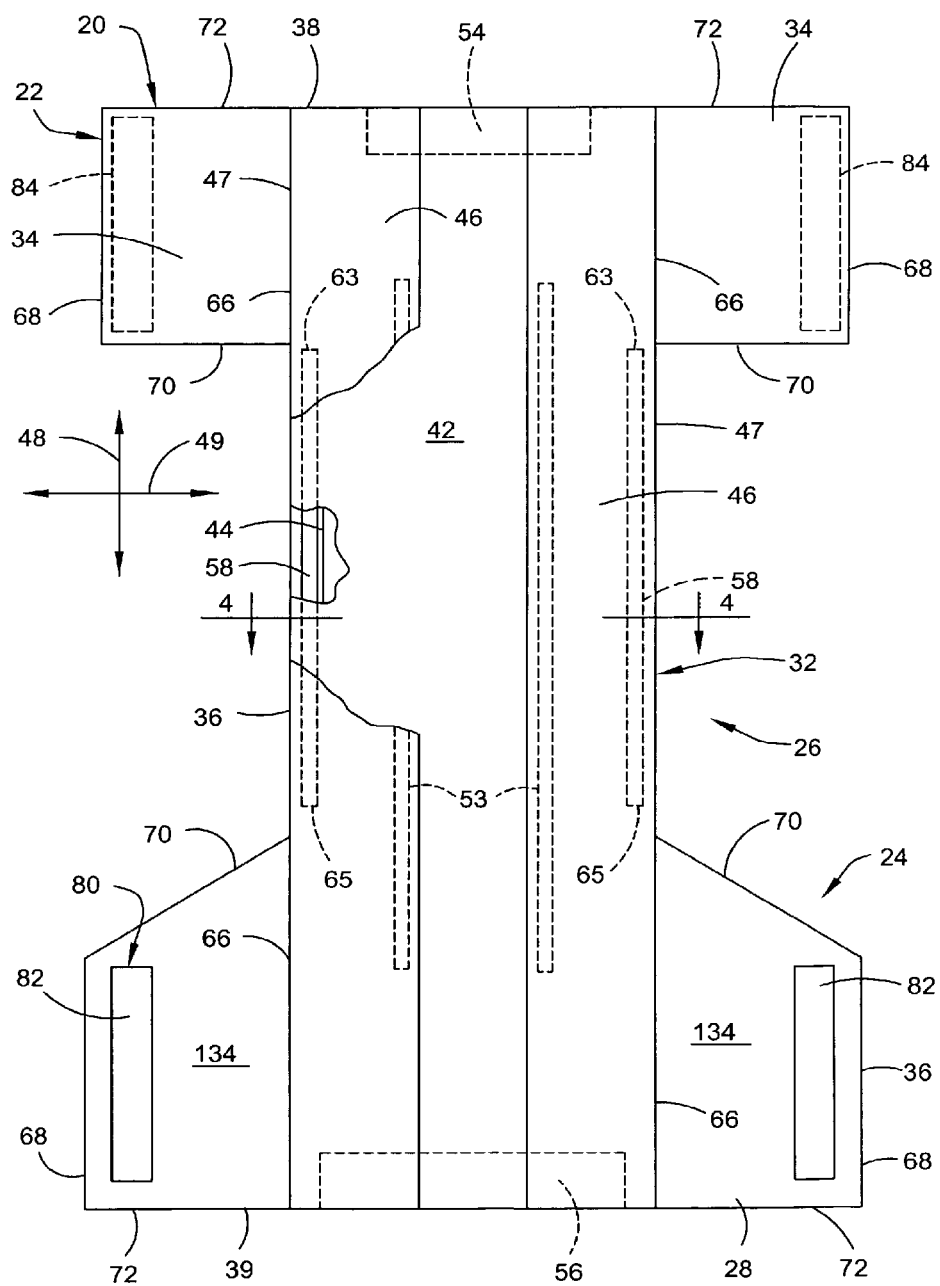
FIG. 3 is a top plan view similar to FIG. 2 showing the surface of the training pants that faces the wearer when worn and with portions cut away to show underlying features.

Still referring to FIGS. 1-3, the central absorbent assembly 32 comprises an outer cover 40 (broadly, a substrate) and a bodyside liner 42 (FIGS. 1 and 3) (also broadly referred to as a substrate) attached to the outer cover in superposed relation therewith by adhesive, ultrasonic bonds, thermal bonds or other conventional techniques. The liner 42 is suitably adapted (i.e., positioned relative to the other components of the pants 20) for contiguous relationship with the wearer's skin when the pants are worn. The absorbent assembly 32 further comprises an absorbent composite 44 (FIG. 3) disposed between the outer cover 40 and the bodyside liner 42 for absorbing liquid body exudates exuded by the wearer. A pair of containment flaps 46 (FIG. 3) is secured to the bodyside liner 42 to inhibit the lateral flow of body exudates.

The central absorbent assembly 32 of the illustrated embodiment has opposite ends which form portions of the front and back waist edges 38 and 39, and opposite side edges 47 which form portions of the side edges 36 of the training pants 20 (FIGS. 2 and 3). For further reference, arrows 48 and 49 depict the orientation of the longitudinal axis and the transverse or lateral axis, respectively, of the training pants 20.

With the training pants 20 fastened as is partially illustrated in FIG. 1, the front and back side panels 34, 134 are connected together by a fastening system 80 in a three-dimensional configuration of the pants to define a waist opening 50 and a pair of leg openings 52 of the pants. In such a configuration, the front and back side panels 34 and 134 constitute those portions of the training pants 20 which are positioned on the hips of the wearer. The front and back waist edges 38 and 39 of the training pants 20 are configured to encircle the waist of the wearer to define the waist opening 50 (FIG. 1) of the pants. The laterally opposite side edges 36 of the pants 20 define the leg openings 52 of the pants.

In the illustrated embodiment, the containment flaps 46 each have at least one flap elastic member 53 (FIG. 3) secured thereto along an unattached edge of the flap so that the flaps assume a generally upright configuration in at least the crotch region 26 of the training pants 20 to form a seal against the wearer's body. The containment flaps 46 are suitably located adjacent the side edges 36 of the pants 20, and can extend longitudinally along the entire length of the absorbent assembly 32 or may extend only partially along the length of the absorbent assembly. Suitable constructions and arrangements for the containment flaps 46 are generally well known to those skilled in the art and are described in U.S. Pat. No. 4,704,116 issued Nov. 3, 1987 to Enloe, which is incorporated herein by reference. It is also contemplated that the containment flaps 46 may be omitted without departing from the scope of this invention.

Figure 4:
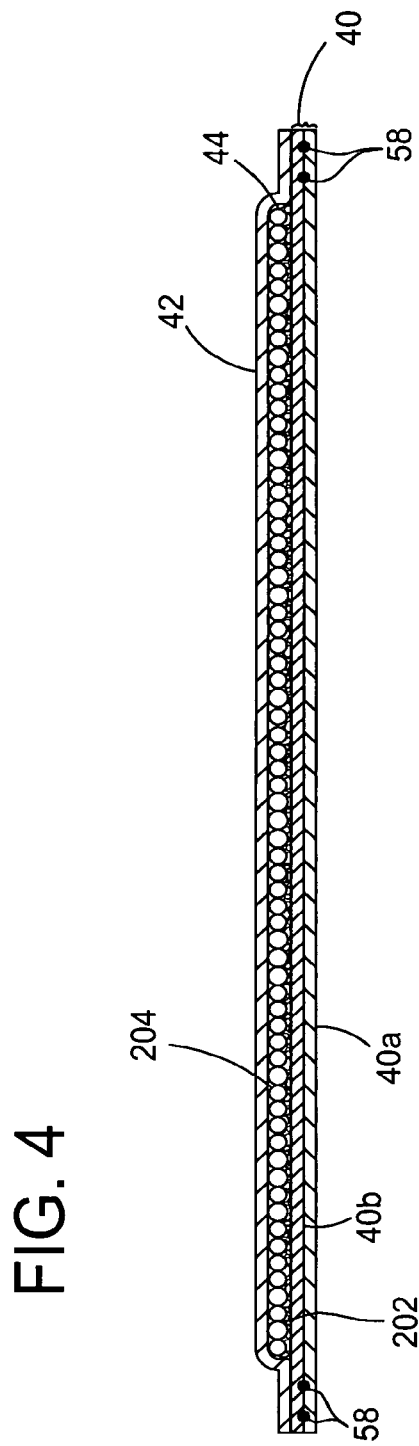
FIG. 4 is a schematic cross-section taken in the plan of line 4-4 of FIG. 3 with containment flaps of the pants omitted.

The training pants 20 also suitably includes a front waist elastic member 54 (FIG. 3), a rear waist elastic member 56, and leg elastic members 58, as are known to those skilled in the art. The waist elastic members 54 and 56 can be operatively joined to the outer cover 40 and/or the bodyside liner 42 along the opposite waist edges 38 and 39, and can extend laterally across all or only a portion of each waist edge. The leg elastic members 58 can be operatively joined to the outer cover 40 (e.g., between the inner and outer layers of the outer cover as shown in FIG. 4) and/or the bodyside liner 42 and extend longitudinally adjacent the opposite side edges 36 generally at the crotch region 26 of the training pants 20. Each leg elastic member 58 has a front terminal point 63 and a back terminal point 65, which represent the longitudinal ends of the elastic gathering caused by the leg elastic members.

The flap elastic members 53, the waist elastic members 54 and 56, and the leg elastic members 58 can be formed of any suitable elastic material. Suitable elastic materials include sheets, strands or ribbons of natural rubber, synthetic rubber, or thermoplastic elastomeric polymers. The elastic materials can be stretched and adhered to a substrate (e.g., such as the outer cover 40 and/or the bodyside liner 42), adhered to a gathered substrate, or adhered to a substrate and then elasticized or shrunk, such as upon the application of heat, so that elastic retroactive forces are imparted to the substrate. In one particularly suitable embodiment, for example, the leg elastic members 58 may comprise a plurality of dry-spun coalesced multifilament spandex elastomeric threads commercially available under the trade name LYCRA® from E.I. Du Pont de Nemours and Company, Wilmington, Del., U.S.A.

The side panels 34, 134 can be permanently secured along seams 66 to the central absorbent assembly 32 in the respective front and back waist regions 22 and 24. More particularly, as seen best in FIGS. 2 and 3, the front side panels 34 can be permanently secured to and extend transversely outward beyond the side edges 47 of the absorbent assembly 32 at the front waist region 22, and the back side panels 134 can be permanently secured to and extend transversely outward beyond the side edges of the absorbent assembly at the back waist region 24. The side panels 34, 134 may be bonded to the absorbent assembly 32 using adhesive, or by thermal or ultrasonic bonding, or by other suitable securement techniques. Alternatively, the side panels 34, 134 may be formed integrally with, or otherwise replaced in part or in whole by, a stretchable outer cover constructed as described later herein, whereby the stretchability of the outer cover contributes to the elastomeric properties required for fit an function. In other alternative embodiments, the side panels 34, 134 may be formed integrally with the bodyside liner 42 and/or another component of the absorbent assembly 32.

The front and back side panels 34, 134 each have an outer edge 68 spaced laterally from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the absorbent assembly 32 to the outer edges 68. The leg end edges 70 of the side panels 34 and 134 form part of the side edges 36 of the training pants 20. The leg end edges 70 of the illustrated embodiment are suitably curved and/or angled relative to the transverse axis 49 to provide a better fit around the wearer's legs. However, it is understood that only one of the leg end edges 70 may be curved or angled, such as the leg end edge of the back waist region 24, or neither of the leg end edges may be curved or angled, without departing from the scope of this invention. The waist end edges 72 are suitably parallel to the transverse axis 49. The waist end edges 72 of the front side panels 34 form part of the front waist edge 38 of the training pants 20, and the waist end edges 72 of the back side panels 134 form part of the back waist edge 39 of the pants.

The side panels 34, 134 suitably, although not necessarily, comprise an elastic material capable of stretching in a direction generally parallel to the transverse axis 49 of the training pants 20. Suitable elastic materials, as well as one process of incorporating elastic side panels into training pants, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular embodiments, suitable elastic materials from which the side panels 34, 134 may be constructed may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference. Alternatively, the side panel material may comprise other woven or non-woven materials, such as those described later herein as being suitable for construction of the outer cover 40 and/or the bodyside liner 42; mechanically pre-strained composites; or extensible but non-stretchable (e.g., inelastic) materials.

The fastening system 80 comprises laterally opposite first fastening components 82 adapted for refastenable engagement to corresponding second fastening components 84. In one embodiment, a front or outer surface of each of the fastening components 82, 84 comprises a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 can comprise any refastenable fasteners suitable for absorbent articles, such as adhesive fasteners, cohesive fasteners, mechanical fasteners, or the like. In particular embodiments the fastening components 82, 84 comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated embodiment, the first fastening components 82 comprise loop fasteners and the second fastening components 84 comprise complementary hook fasteners. Alternatively, the first fastening components 82 may comprise hook fasteners and the second fastening components 84 may comprise complementary loop fasteners. In another embodiment, the fastening components 82, 84 can comprise interlocking similar surface fasteners, or adhesive and cohesive fastening elements such as an adhesive fastener and an adhesive-receptive landing zone or material; or the like. Although the training pants 20 illustrated in FIG. 1 show the back side panels 134 overlapping the front side panels 34 upon connection thereto, which is convenient, the training pants 20 can also be configured so that the front side panels overlap the back side panels when connected. One skilled in the art will recognize that the shape, density and polymer composition of the hooks and loops may be selected to obtain the desired level of engagement between the fastening components 82, 84. A more aggressive hook material may comprise a material with a higher modulus and/or a material having a greater percentage of directionally-aligned hooks. When engaged, the fastening components 82, 84 of the illustrated embodiment define refastenable engagement seams 85 (FIG. 1).

In the illustrated embodiment, the fastening components 82, 84 are shown as being formed separate from the side panels 34, 134 and secured thereto, such as by adhesive, thermal or ultrasonic bonding, or other suitable technique. However, it is contemplated that one or both of the fastening components 82, 84 may be formed integrally with the respective side panels 34, 134 or other components (e.g., the outer cover 40 or liner 42) of the pants 20 without departing from the scope of this invention. It is also contemplated that the pants 20 may be permanently joined at the engagement seams 85, such as by adhesive, thermal or ultrasonic bonding, or other suitable technique.

The outer cover 40 is substantially liquid impermeable to inhibit body exudates against leaking from the pants 20 and wetting articles, such as bed sheets and clothing, as well as the wearer and caregiver. The outer cover 40 may be constructed of a single layer of liquid impermeable material or more suitably it may be a multi-layered laminate structure in which at least one of the layers is liquid impermeable. For instance, as shown in FIG. 4, the outer cover 40 can include a liquid permeable outer layer 40a and a liquid impermeable inner layer 40b joined together by a laminate adhesive, or by ultrasonic bonds, thermal bonds, or the like. In such an embodiment, the inner layer of the outer cover 40 can be both liquid and vapor impermeable, or it may be liquid impermeable and vapor permeable. For example, the inner layer 40b can be manufactured from a thin plastic film, although other flexible liquid impermeable materials may be used.

Alternative constructions of the outer cover 40 may comprise a woven or non-woven fibrous web layer which has been totally or partially constructed or treated to impart the desired levels of liquid impermeability to selected regions that are adjacent or proximate the absorbent composite. For example, the outer cover may include a gas-permeable, non-woven fabric layer laminated to a polymer film layer which may or may not be gas-permeable. Other examples of fibrous, cloth-like outer cover materials can comprise a stretch thinned or stretch thermal laminate material.

In a particularly suitable embodiment, the outer cover 40 is stretchable, and even more suitably the outer cover is elastic. As used herein, the term "stretchable" refers to a material that may be extensible and/or elastic. That is, the material may be extended, deformed or the like, without breaking, and may or may not significantly retract after removal of an extending force. The terms "elastic" and "elastomeric" as used herein refer to a material which, upon application of an elongating force, is elongatable in at least one direction and retracts to dimensions close to its original dimensions (e.g., within at least about 25 percent) upon removal of the elongating force. For example, an elastic material elongated by an elongating force to a length which is at least 50 percent greater than the relaxed, unelongated length of the material will recover to within at least about 25 percent of its relaxed, unelongated length within a short period of time (e.g., about one minute) following removal of the elongating force. As a hypothetical example, a one inch (2.54 centimeters (cm)) long sample of an elastic material which is elongatable under an elongating force to at least about 1.5 inches (3.81 cm) will recover to a length of not more than about 1.375 inches (3.5 cm) within one minute following removal of the elongating force. The term "extensible" refers to that property of a material where upon removal of an elongating force, the material experiences a substantially permanent deformation or the material does not exhibit a significant retractive force.

As an example, the outer cover 40 may be composed of a single layer, multiple layers, laminates, spunbond fabrics, films, meltblown fabrics, elastic netting, microporous web, bonded carded webs or foams comprised of elastomeric or polymeric materials. Elastomeric non-woven laminate webs may include a non-woven material joined to one or more gatherable non-woven webs, films, or foams. Stretch bonded laminates (SBL) and neck bonded laminates (NBL) are examples of elastomeric composites. Examples of suitable non-woven materials are spunbond-meltblown fabrics, spunbond-meltblown-spunbond fabrics, spunbond fabrics, or laminates of such fabrics with films, foams, or other non-woven webs.

Suitable elastomeric materials may include cast or blown films, foams, or meltblown fabrics composed of elastomeric polyethylene, polypropylene, or polyolefin copolymers, as well as combinations thereof. The elastomeric materials may include PEBAX® elastomer (available from AtoChem located in Philadelphia, Pa.), HYTREL® elastomeric polyester (available from E.I. DuPont de Nemours located in Wilmington, Del.), KRATON® elastomer (available from Kraton Polymers of Houston, Tex.), or strands of LYCRA® elastomer (available from E.I. DuPont de Nemours located in Wilmington, Del.), or the like, as well as combinations thereof. The outer cover 40 may include materials that have elastomeric properties through a mechanical process, a printing process, a heating process, and/or a chemical treatment. For examples such materials may be apertured, creped, neck-stretched, heat activated, embossed, and micro-strained.

The bodyside liner 42 presents a body-facing surface which isolates the wearer's skin from liquids retained by the absorbent composite 44, and is suitably compliant, soft-feeling, and non-irritating to the wearer's skin. Further, the bodyside liner 42 can be less hydrophilic than the absorbent composite 44, and is sufficiently porous to be liquid permeable, permitting liquid to readily penetrate through its thickness to reach the absorbent composite. A suitable bodyside liner 42 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers.

Various woven, knitted and non-woven fabrics can be included in the bodyside liner 42. For example, the bodyside liner 42 may include a meltblown web, a spunbond web, or a bonded-carded-web composed of the desired fibers. The various fabrics can be composed of natural fibers, synthetic fibers or combinations thereof. In particular aspects, the bodyside liner 42 may be comprised of polymer fibers, networks, laminates, liquid permeable films, cellulosic fibers, rayon, water swellable gels, and elastomeric materials, as well as combinations thereof. Suitable materials for the bodyside liner can include meltblown webs, airlaid webs, spunbond webs, or bonded-carded webs of synthetic continuous or discrete polymer fibers and/or natural fibers, a pattern bonded spunbonded web, airlaid web, or bonded carded web, as well as combinations thereof. Suitable polymers can include polypropylene, polyethylene, polyester, nylon and bicomponent and biconstituent materials composed of these polymers.

The bodyside liner may be composed of a substantially hydrophobic material, and the hydrophobic material may optionally be treated with a surfactant or otherwise processed to impart a desired level of wettability and hydrophilicity. For example, in one embodiment the bodyside liner 42 can be a non-woven, spunbond polypropylene fabric which is necked to approximately 40% of its original width. Strands of KRATON® G2760 elastomer material may be adhered to the necked spunbond material. The fabric can be surface treated with an operative amount of surfactant, such as about 0.45% AHCOVEL® Base N62 surfactant, available from Uniqema, a division of ICI, a business having offices located in New Castle, Del. The surfactant can be applied by any conventional means, such as spraying, printing, brush coating or the like.

In a particularly suitable embodiment, the bodyside liner 42 is stretchable, and more suitably the liner is elastic in correspondence with the outer cover 40. The stretchable bodyside liner 42 can include elastic strands or netting, LYCRA® elastics, cast or blown elastic films, non-woven elastic webs, meltblown or spunbond elastomeric fibrous webs, as well as combinations thereof. Examples of suitable elastomeric materials include KRATON® elastomers, HYTREL® elastomers, ESTANE® elastomeric polyurethanes (available from B.F. Goodrich and Company located in Cleveland, Ohio), PEBAX® elastomers, and elastomeric polyolefins such as Vistamaxx (available from Exxon Mobil Corporation of Irving, Tex.), AFFINITY® (available from Dow Chemical of Midland, Mich.), and the like. The bodyside liner 42 may include blends or laminates of fibers, scrim, webs, necked webs and films with perforations, apertures, creping, heat activation, embossing, micro-straining, chemical treatment, or the like, as well as combinations thereof including homofilaments, bicomponent filaments of the sheath/core or side-by-side configuration, or biconstituent filaments comprising blends of polymers, wherein the composite filaments exhibit elastic properties. It is contemplated as an alternative that the bodyside liner 42 may be stretchable while the outer cover 40 is non-stretchable without departing from the scope of this invention. It is also contemplated that the liner 42 may be extensible instead of elastic.

The bodyside liner 42 and outer cover 40 are suitably attached to one another, for example, by being directly attached to each other such as by affixing the outer cover 40 directly to the liner 42, or by being indirectly attached to each other such as by affixing the bodyside liner to intermediate components of the pants 20 which in turn are affixed to the outer cover. The bodyside liner 42 and the outer cover 40 can, for example, be attached to each other along at least a portion of their periphery by adhesive, by ultrasonic bonding, by thermal bonding or by other suitable attachment techniques known in the art. It should be readily appreciated that the above-described attachment techniques may also be employed to suitably interconnect, assemble and/or affix together various other component parts of pants 20 described herein.

The absorbent composite 44 is generally conformable and non-irritating to the wearer's skin and is suitably constructed to absorb and retain liquid body exudates. With particular reference to FIG. 4, in accordance with one embodiment of the present invention the absorbent composite 44 is formed on the outer cover 40 and comprises a layer 202 of adhesive composition adhered to the inner layer 40b of the outer cover 40 and a layer 204 of particulate superabsorbent material adhered to the adhesive composition.

As used herein, the term "superabsorbent material" refers to a water-swellable, water-insoluble organic or inorganic material capable, under the most favorable conditions, of absorbing at least about ten times its weight and, more desirably, at least about thirty times its weight in an aqueous solution containing 0.9 weight percent sodium chloride. The superabsorbent material can be selected from natural, synthetic, and modified natural polymers and materials. The superabsorbent material can comprise inorganic materials, such as silica gels, or organic compounds, such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces. Examples of suitable synthetic superabsorbent material polymers include the acidic or alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), or basic or chloride and hydroxide salts of polyvinyl amine, polyamine polyquarternary ammonium, polyimine, hydrolyzed polyamide, and mixtures and copolymers thereof.

Other suitable superabsorbent material polymers include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Additional suitable superabsorbent materials are disclosed in U.S. Pat. No. 3,901, 236 issued Aug. 26, 1975 and processes for preparing synthetic absorbent gelling polymers are disclosed in U.S. Pat. No. 4,076,663 issued Feb. 28, 1978 and U.S. Pat. No. 4,286, 082 issued Aug. 25, 1981.

Suitable superabsorbent materials are commercially available from various suppliers. For example, SXM 9543 and FAVOR 880 are suitable superabsorbent materials available from Stockhausen, Inc. of Greensboro, N.C., U.S.A.; and DRYTECH 2035 is a suitable superabsorbent material available from Dow Chemical Company of Midland, Mich., U.S.A. Another suitable superabsorbent material is a multi-component superabsorbent particulate gel from BASF of Ludwigshafen, Germany designated E1231-99. This superabsorbent material has a fecal fluid Absorbency Under Load (AUL) at 0.3 psi of 27.1 grams/gram and a saline AUL at 0.3 psi of 33.0 grams/gram. Multicomponent superabsorbent gel particles and methods to prepare them are described in U.S. Pat. Nos. 5,981,689; 6,072,101; 6,087,448; 6,121,409; 6,159, 591; 6,194,631; 6,222,091; 6,235,965; 6,342,298; 6,376,072; 6,392,116; 6,509,512; and 6,555,502; U.S. Patent Publications 2001/01312; 2001/07064; 2001/29358; 2001/44612; 2002/07166; 2002/15846; and 2003/14027; and PCT Publications WO 99/25393; WO 99/25745; WO 99/25748; WO 00/56959; WO 00/63295; WO 02/10032; WO 03/18671; and WO 03/37392; the disclosures of which are incorporated by reference to the extent they are consistent herewith.

The superabsorbent material particles used in forming the absorbent composite 44 can be of any desired configuration, such as spiral or semi-spiral, cubic, rod-like, polyhedral, random, spherical (e.g., beads), needles, flakes, and fibers. Conglomerates of particles of superabsorbent material may also be used in forming the absorbent composite 44. As an example, in a particularly suitable embodiment the superabsorbent material particles have an average particle size in the range of from about 20 micrometers to about 1 millimeter. "Particle size" as used herein means the weighted average of the smallest dimension of the individual particles.

In one embodiment, the adhesive composition is suitably a hot-melt adhesive. Such an adhesive generally comprises one or more polymers to provide cohesive strength (e.g., aliphatic polyolefins such as poly (ethylene-co-propylene, polyamides, polyesters, and/or polyether blends) copolymer; ethylene vinyl acetate copolymers; styrene-butadiene or styrene-isoprene block copolymers; etc.); a resin or analogous material (sometimes called a tackifier) to provide adhesive strength (e.g., hydrocarbons distilled from petroleum distillates; rosins and/or rosin esters; terpenes derived, for example, from wood or citrus, etc.); perhaps waxes, plasticizers or other materials to modify viscosity (i.e., flowability) (examples of such materials include, but are not limited to, mineral oil, polybutene, paraffin oils, ester oils, and the like); and/or other additives including, but not limited to, antioxidants or other stabilizers.

As an example, the hot-melt adhesive may contain from about 15 to about 50 weight percent cohesive strength polymer or polymers; from about 30 to about 65 weight percent resin or other tackifier or tackifiers; from more than zero to about 30 weight percent plasticizer or other viscosity modifier; and optionally less than about 1 weight percent stabilizer or other additive. It should be understood that other hot-melt adhesive formulations comprising different weight percentages of these components are possible. It is also contemplated the adhesive composition may either be hydrophilic or hydrophobic without departing from the scope of this invention.

In a particularly suitable embodiment, the adhesive composition has a viscosity of less than about 10,000 centipoises (cps) at a temperature of less than or equal to about 400 degrees Fahrenheit (204 degrees Celsius), more suitably at a temperature of less than or equal to about 300 degrees Fahrenheit (149 degrees Celsius), and still more suitably at a temperature of less than or equal to about 250 degrees Fahrenheit (121 degrees Celsius). In another embodiment, the adhesive composition suitably has a viscosity in the range of about 1,000 cps to about 8,000 cps at a temperature of about 300 degrees Fahrenheit (149 degrees Celsius), and still more suitably in the range of about 2,000 cps to about 6,000 cps at a temperature of about 300 degrees Fahrenheit (149 degrees Celsius).

As used herein, the "viscosity" of the composition is defined as the viscosity determined using the Viscosity Test set forth later herein. Using a relatively low viscosity adhesive composition promotes sufficient contact with (e.g., coating of) the particulate superabsorbent material, thereby more readily capturing and holding the superabsorbent material particles.

Low viscosity adhesive compositions can be processed, i.e., melted and applied to the outer cover 40 or other pants components as will be described later herein, at lower processing temperatures, thereby promoting ease of manufacturing. A lower processing temperature also reduces the risk of thermal degradation of the substrate (e.g., the outer cover 40) on which the absorbent composite 44 is formed. As an example, the adhesive composition is suitably processable at temperatures in the range of about 200 degrees Fahrenheit (93 degrees Celsius) to about 400 degrees Fahrenheit (204 degrees Celsius), and more suitably in the range of about 250 to about 360 degrees Fahrenheit (about 121 to about 182 degrees Celsius).

The adhesive composition also has a suitably low storage modulus (G'). The storage modulus of the adhesive composition generally refers to the ability of the adhesive composition (after it has set up or otherwise generally dried, e.g., after cooling) to deform, such as upon flexing of the outer cover 40 or other substrate on which the absorbent composite 44 is formed, without a substantial loss of integrity of the adhesive composition. By using an adhesive composition having a relatively low storage modulus, the absorbent composite 44 formed on the outer cover 40 is suitably generally soft and flexible to permit flexing of the composition along with the outer cover. More specifically, the storage modulus is a coefficient of elasticity representing the ratio of stress to strain as the adhesive composition is deformed under a dynamic load.

As used herein, the storage modulus of the adhesive composition is reported as measured according to the Rheology Test set forth in detail later herein. As an example, the storage modulus (G') of the adhesive composition as determined by the Rheology Test is suitably less than or equal to about $1.0 \times 10^7$ dyne/cm$^2$ at 25 degrees Celsius, is more suitably in the range of about $1.0 \times 10^4$ to about $1.0 \times 10^7$ dyne/cm$^2$ at 25 degrees Celsius, and is still more suitably in the range of about $1.0 \times 10^5$ to about $1.0 \times 10^6$ dyne/cm$^2$ at 25 degrees Celsius.

The adhesive composition also suitably has a glass transition temperature (Tg) in the range of about −25 to about 25 degrees Celsius, and more suitably in the range of about −10 to about 25 degrees Celsius. The "glass transition temperature" as used herein refers generally to the molecular mobility of the adhesive composition. For example, where the temperature of the adhesive composition is below the glass transition temperature (Tg), it tends to more rigid and brittle, and where the temperature of the composition is above the glass transition temperature (Tg) the composition has more of a tendency to flow. However, in the event that the adhesive composition temperature substantially exceeds the glass transition temperature (Tg) of the composition, the composition can have substantially reduced adhesive properties. Thus, the glass transition temperature of the adhesive composition is suitably close the temperature at which the composition is to be used (e.g., room temperature). The glass transition temperature (Tg) of the adhesive composition as used herein refers to the glass transition temperature as measured by the Rheology Test set forth later herein.

Some examples of suitable adhesive composition for use in forming the absorbent composite 44 are hot-melt adhesives commercially available from National Starch and Chemical Co. of Bridgewater, N.J., under the designations 34-5610 and 34-447A. Other examples of suitable adhesive compositions are those made by Bostik-Findley in Milwaukee, Wis. under the designations HX 4207-01, HX 2773-01, H2525A and H2800. Other suitable adhesive compositions may alternatively, or additionally, be used without departing from the scope of this invention. Moreover, the term "adhesive composition" as used herein is not intended to exclude materials, substances, compositions and the like designated by a term other than "adhesive" or "adhesive composition" but having the characteristics of and functioning in accordance with the adhesive compositions described herein.

Experiment 1

The hot-melt adhesives identified above as HX 4207-01, HX 2773-01, and 34-5610 were subjected to the Viscosity Test described later herein to determine the viscosity, in centipoises (cps) of the adhesive composition at temperatures of 250, 275, 300, 325 and 350 degrees Fahrenheit (respectively, 121, 135, 149, 163 and 177 degrees Celsius). The results of the Viscosity Test were as follows:

| Temperature (Degrees Fahrenheit) | HX 4207-01 Viscosity (cps) | HX 2773-01 Viscosity (cps) | 34-5610 Viscosity (cps) |
|---|---|---|---|
| 250 | 7,925 | 7,437 | 19,100 |
| 275 | 3,887 | 3,587 | 9462 |
| 300 | 2,155 | 1,990 | 5412 |
| 325 | 1,300 | 1,197 | 3275 |
| 350 | 843 | 758 | 2175 |

Experiment 2

The hot-melt adhesives identified above as HX 4207-01, HX 2773-01, H2525A, 34-5610 and 34-447A were subjected to the Rheology Test described later herein to determine the storage modulus (G') at 25 degrees Celsius, in dynes/square centimeter, and the glass transition temperature (Tg), in degrees Celsius, for each of the adhesive compositions. The results of the Rheology Test are set forth below.

| Adhesive | G' at 25 degrees C. ($\times 10^5$ dynes/cm$^2$) | Tg (degrees C.) |
|---|---|---|
| HX 4207-01 | 5.26 | 20.0 |
| HX 2773-01 | 4.34 | 19.2 |
| H2525A | 9.8 | 20.6 |
| 34-5610 | 5.0 | 12.5 |
| 34-447A | 0.971 | −8.84 |

In accordance with one embodiment of a method of the present invention for making an absorbent article, such as the pants 20, the absorbent composite 44 is formed directly on the outer cover 40 (or other substrate) by first applying a layer (e.g., layer 202 of FIG. 4) of adhesive composition to the inner layer 40b of the outer cover. For example, with reference to FIG. 6, the adhesive composition may be applied to a moving web 222 of substrate material (e.g., outer cover 40 material) by a suitable adhesive applicator, generally indicated at 220. The applicator 220 generally comprises a main control system 224 operatively connected to an adhesive flow-control system 226 for controlling the delivery of the adhesive composition in generally liquid form to the moving web 222.

The adhesive composition may be supplied to a heating tank 228 of the applicator in solid form, such as pellets, blocks, or some other shape, and is then heated in the tank so that the adhesive composition is in a flowable (e.g., generally liquefied) form. The flowable adhesive composition is transported from the tank 28 via a pump (e.g., a gear pump or positive-displacement pump, not shown) to a metering mechanism 232. The metering mechanism 232 is configured to deliver the adhesive composition to one or more nozzles, such as nozzles 238, 240 of FIG. 6, depending upon the number of nozzles required to provide the desired pattern of adhesive composition on the moving web 222.

The adhesive composition is then blown from the nozzles 238, 240 in a high velocity stream of gas, such as air, onto the moving web 222. The blown adhesive composition is generally fibrous, such as in the form of discrete fibers or filaments. For example, the resulting adhesive composition fibers may have a fiber diameter in the range of about 5 microns to about 200 microns, and more suitably in the range of about 7 microns to about 50 microns. Upon application to the moving web 222, the blown adhesive composition fibers form a random laid fibrous layer of adhesive on the web material.

The nozzles 238, 240 can be any device capable of providing the desired pattern of adhesive on the moving web 222. Some examples of suitable nozzles include those commercially available from Nordson Corporation of Duluth, Ga., U.S.A., under respective trade designations MB200 and CC-200 Controlled Coat, which are configured to deliver the adhesive composition in a generally random spray pattern. Another example of a suitable nozzle is also available from Nordson Corporation under the trade designation CF-200 Controlled Fiberization) and is configured to deliver the adhesive composition in a generally swirl pattern. Yet another suitable nozzle is available from ITW Dynatec Co. of Hendersonville, Tenn., U.S.A., under the trade designation UFD (Uniform Fiber Deposition) and also provides a random spray pattern of adhesive composition. It is understood that other nozzles may be used to provide spray patterns other than a random spray pattern or a swirl pattern, such as slot coated patterns, spot coated patterns and/or continuous bead line patterns, without departing from the scope of this invention.

The adhesive applicator 220 described to this point is well known to those skilled in the art and will not be further described herein except to the extent necessary to describe the present invention. It is understood that other applicators or devices may suitably be used to apply a layer 202 of adhesive composition to a substrate, such as the outer cover 40, without departing from the scope of this invention. In one embodiment, the layer 202 of adhesive composition formed on the outer cover 40 suitably has a basis weight in the range of about 1 to about 100 grams per square meter (gsm), and more suitably in the range of about 4 to about 50 gsm. In another embodiment, the amount of adhesive used in forming the absorbent composite is suitably less than or equal to about 15 percent by weight of the amount of superabsorbent material used in forming the absorbent composite, and more suitably in the range of about 5 to about 10 weight percent of the amount of superabsorbent material used.

After applying a layer 202 (FIG. 4) of adhesive composition to the substrate, the web 222 of substrate material is moved past a suitable device (not shown) for applying a layer 204 of particulate superabsorbent material to the adhesive composition. For example, in one suitable embodiment the device comprises a source of particulate superabsorbent material and a source of pressurized air for delivering the particulate superabsorbent material in a stream of high velocity air from the source thereof onto the moving web, i.e., into contact with the layer 202 of adhesive composition. Such devices are well known in the art and will not be further described herein except to the extent necessary to disclose the present invention. For example, devices which are typically used in a conventional coform process to deliver superabsorbent material onto a moving conveyor may be used. Such devices are disclosed, for example, in U.S. Pat. No. 4,724,114, the disclosure of which is incorporated herein by reference.

It is contemplated that the particulate superabsorbent material may be delivered onto the layer 202 of adhesive other than by high velocity air, such as gravimetrically, i.e., by being dropped onto the layer of adhesive. It is also contemplated that the particulate superabsorbent material may be directed toward the moving web in a stream of high velocity air wherein the stream intersects (e.g., merges or mixes with) the stream of adhesive composition so that the adhesive fibers and superabsorbent material particles mix before contacting the web 222 such as in the manner of a conventional coform process. One example of a coform process is disclosed in U.S. Pat. No. 4,724,114. In such an embodiment, the absorbent composite 44 formed on the substrate comprises a more blended or commingled mixture instead of the generally layered arrangement shown in FIG. 4.

The article (e.g., the substrate and absorbent composite formed thereon) may then be subjected to further processing. For example, another substrate material, e.g., the material from which the liner 42 is constructed, may be laid over the absorbent composite 44 and attached to the moving web of substrate (e.g., outer cover 40) material. In one embodiment the outer cover 40 and the absorbent composite 44 formed thereon (and, optionally, the bodyside liner 42) may be passed through opposed nip rolls (not shown) to apply a compressive force thereto to facilitate strengthening of the bonds between the adhesive composition and the outer cover as well as between the particulate superabsorbent material and the adhesive composition. The compression may also reduce the thickness, or caliper of the absorbent composite. The outer cover 40 and absorbent composite 44 (and, optionally, the liner 42) may also be cut to a desired shape for the pants 20 or other article.

In a particularly suitable embodiment, the adhesive composition has a relatively long open time. As used herein, the "open time" of the adhesive composition refers to the length of time during which an adhesive composition remains tacky or sticky. More suitably, the open time of the adhesive composition is sufficiently long so that the adhesive composition is still tacky upon application of the superabsorbent material particles thereto, and more suitably it remains tacky prior to the outer cover and the absorbent composite formed thereon passing through the nip rolls. The compressive force applied by the nip rolls thus facilitates the flow and/or deformation of the adhesive composition around portions or all of the surface area of the superabsorbent material particles, or presses the particles against the adhesive composition to facilitate better adhesive bonding between the particles and the adhesive composition. As an example, the open time of the adhesive composition is suitably at least about 0.5 seconds and may have an open time as long as the useful life of the pants 20 or other absorbent article in which the adhesive composition is used.

Figure 6:
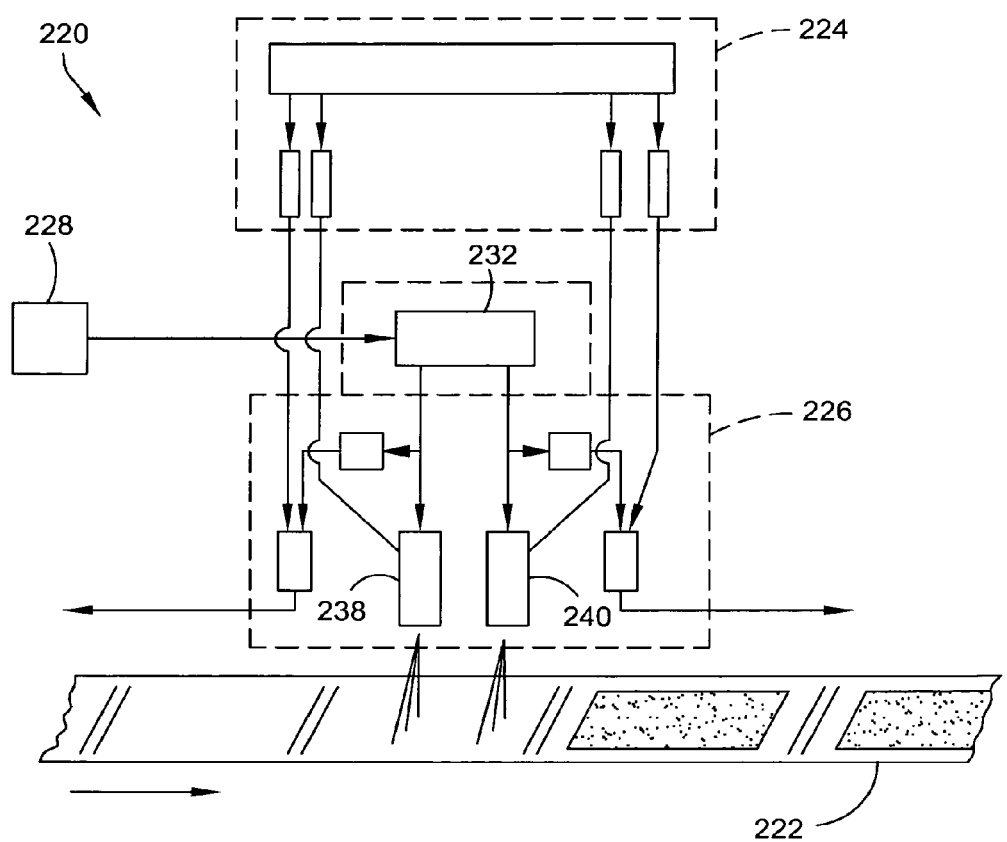
FIG. 6 is a schematic of an adhesive applicator for use in making an absorbent article according to one embodiment of a method of the present invention.

It is also contemplated that the adhesive composition may be applied to the substrate (e.g., the outer cover 40) in a pattern other than the rectangular pattern shown in FIG. 6. For example, the adhesive composition may be applied in a generally hourglass-shaped pattern, an I-shaped pattern, a T-shaped pattern or other suitable pattern depending on the desired shape of the absorbent composite. The substrate may then be cut along the side margins of the absorbent composite in further forming the absorbent article.

In another embodiment, the absorbent composite 44 may alternatively be formed on the bodyside liner 42, and the outer cover 40 may or may not be secured to the absorbent composite without departing from the scope of this invention. It is further contemplated that the absorbent composite may be formed other than directly on a substrate (e.g., the outer cover 40 or liner 42). For example, the absorbent composite may be formed on a moving conveyor belt or other moving or stationary surface. The formed absorbent composite may then be adhered to the outer cover 40, bodyside liner 42 or other substrate while the adhesive composition is still tacky.

Figure 5:
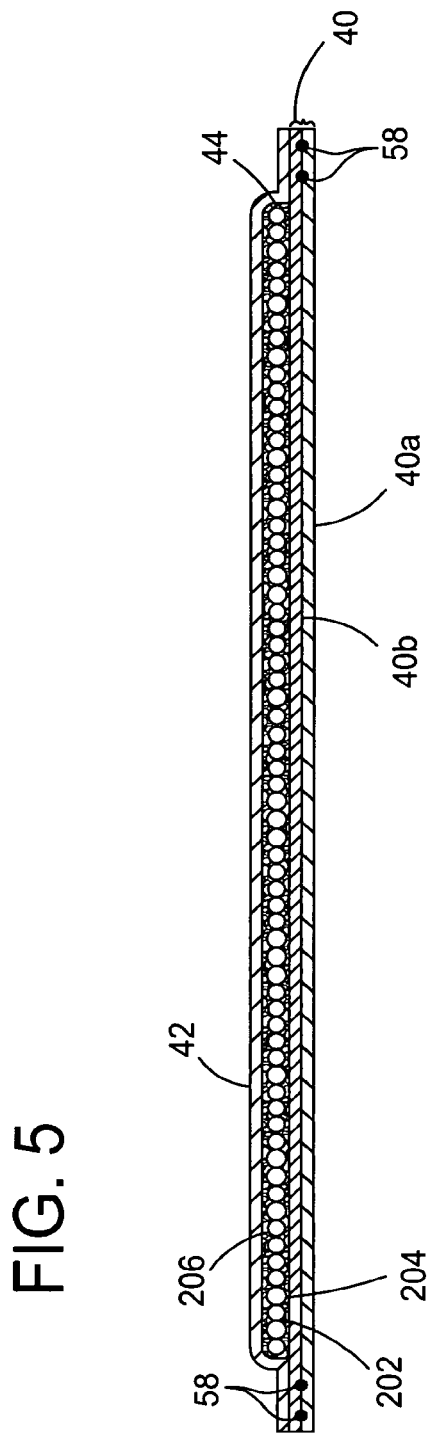
FIG. 5 is a schematic cross-section similar to FIG. 4 but of a second embodiment of an absorbent article of the present invention.

FIG. 5 illustrates another embodiment of the pants 20 in which the absorbent composite 44 further comprises an additional layer 206 of adhesive composition applied to the layer 204 of particulate superabsorbent material to further secure the superabsorbent material particles in the absorbent composite 44. In this embodiment, the absorbent composite 44 is further secured to the liner 42 by the additional layer 206 of adhesive composition.

Figure 7:
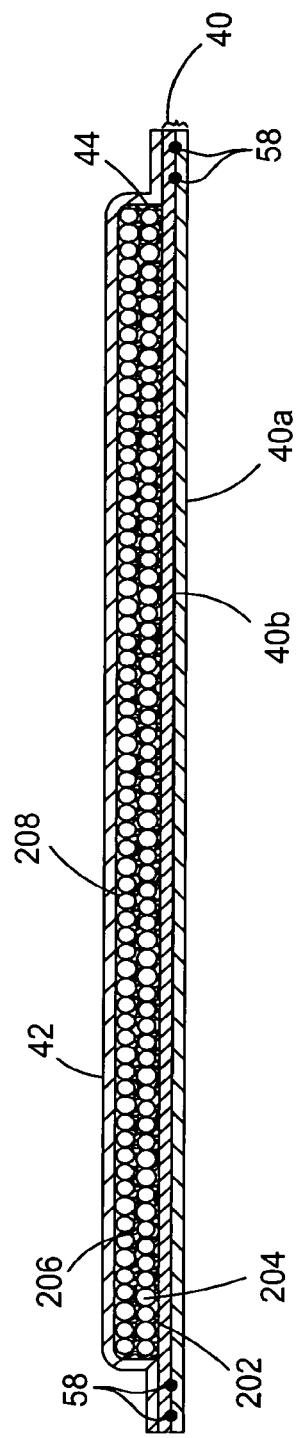
FIG. 7 is a schematic cross-section similar to that of FIG. 4 but of a third embodiment of an absorbent article of the present invention.
Figure 8:
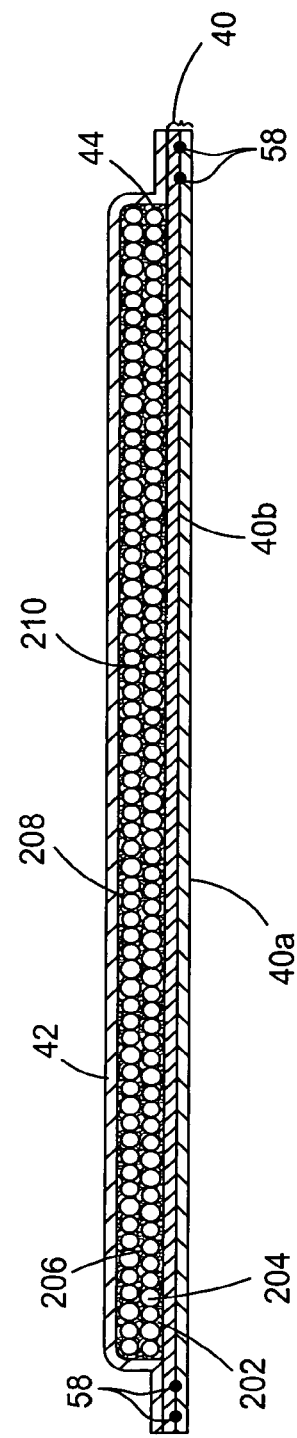
FIG. 8 is a schematic cross-section similar to that of FIG. 4 but of a fourth embodiment of an absorbent article of the present invention.

FIGS. 7 and 8 illustrate additional embodiments in which the absorbent composite 44 comprises multiple layers of both the adhesive composition and the particulate superabsorbent material. In the embodiment of FIG. 7, the absorbent composite 44 is formed on the outer cover 40 and comprises a first layer 202 of adhesive composition applied to the inner layer 40b of the outer cover 40, followed by a first layer 204 of particulate superabsorbent material applied to and held by the first layer of adhesive composition. A second layer 206 of adhesive composition is applied over the first layer 204 of particulate superabsorbent material and then a second layer 208 of particulate superabsorbent material is applied to and held by the second layer of adhesive composition. In FIG. 8, a third layer 210 of adhesive composition is applied over the second layer 208 of particulate superabsorbent material and the liner 42 is secured to the absorbent composite 44 by the third layer of adhesive composition.

The absorbent composite 44 (such as illustrated in FIGS. 7 and 8) comprising multiple layers of both adhesive composition and particulate superabsorbent material suitably has a total basis weight in the range of about 20 gsm to about 1,200 gsm, and more suitably in the range of about 50 gsm to about 800 gsm. The total basis weight of the adhesive composition is suitably in the range of about 1 gsm to about 100 gsm, and more suitably in the range of about 4 gsm to about 50 gsm, and the total basis weight of the particulate superabsorbent material is suitably in the range of about 10 gsm to about 1,150 gsm, and more suitably in the range of about 40 gsm to about 750 gsm.

It is contemplated that the basis weight of one layer of adhesive composition may or may not be the same as that of the other layer or layers of adhesive composition. Likewise, the basis weight of one layer of particulate superabsorbent material may not be same as that of the other layer or layers of particulate superabsorbent material.

It is also understood that the absorbent composite 44 may comprise more than two layers of particulate superabsorbent material and more than three layers of adhesive composition without departing from the scope of this invention. As with the embodiments shown in FIGS. 4 and 5, it also contemplated that the absorbent composites 44 of the illustrated embodiments of FIGS. 7 and 8 may alternatively be formed on the bodyside liner 42 and that the outer cover 40 may or may not be secured to the absorbent composite.

Example 1

A continuous web was made having multiple alternating layers of adhesive composition and superabsorbent material between a pair of substrates in accordance with the absorbent articles and process described above. Each of the substrates was constructed of a bicomponent (sheath/core, with 20 percent by weight polyethylene and 80 percent by weight KRATON elastomer) spunbond web having a basis weight of about 0.8 ounces per square yard (osy) (about 27 grams per square meter, or gsm) and treated with 0.1 percent by weight add on level of a mixture of surfactants (e.g., a 3 to 1 ratio of AHCOVEL surfactant and GLUCOPON surfactant).

The adhesive composition used was that identified above as HX 4207-01 from Bostik Findley of Milwaukee, Wis. The particular superabsorbent material was the SXM 9543 from Stockhausen, Inc. of Greensboro, N.C. A first layer of adhesive composition was applied to one of the substrates, followed by a first layer of superabsorbent material, a second layer of adhesive composition, a second layer of superabsorbent material, a third layer of adhesive composition and then a third layer of superabsorbent material. The other substrate was then placed over the third layer of superabsorbent material in superposed relationship with the substrate onto which the first layer of adhesive composition was applied.

The superabsorbent material layers were applied in generally equal amounts, with the total basis weight of the superabsorbent material being about 357 gsm. The adhesive composition layers were also applied in equal amounts, with the total basis weight of the adhesive composition being about 32 gsm. The total basis weight of the web (e.g., including the two substrates) was about 443 gsm. The width of each of the substrates was about 8.5 inches (21.6 cm) with the absorbent composite having a width of about 7 inches (17.8 cm) and centered laterally between the side edges of the substrates. The edges of the substrates were then cut and removed so that the substrates were flush with the side edges of the absorbent composite, thereby forming the web to have a width of about 7 inches (17.8 cm).

The longitudinal direction of the web coincided with the machine direction of the substrates, e.g., the direction in which the substrates were moving during manufacture thereof. The lateral direction of the web coincided with the cross-machine direction of the substrates, e.g., the direction transverse to the machine direction thereof.

Example 2

A continuous web was made substantially the same as the web of Example 1, but with each of the substrates from which the web was formed instead comprising a bicomponent (sheath/core, with 20 percent polyethylene and 80 percent AFFINITY elastomeric polyethylene from Dow Chemical of Midland, Mich., U.S.A.) spunbond web. This substrate web has a basis weight of about 27 gsm. The superabsorbent material used to form the web of Example 2 was the E1231-99 multicomponent superabsorbent particulate gel from BASF of Ludwigshafen, Germany. The width of the web was formed to be about 7 inches (17.8 cm) in the same manner as the web of Example 1. The superabsorbent material layers had a total basis weight of about 407 gsm. The adhesive composition layers had a total basis of about 37 gsm so that the total basis weight of the web (e.g., including the two substrates) was about 498 gsm. The longitudinal direction of the web coincided with the machine direction of the substrates and the lateral direction of the web coincided with the cross-machine direction of the substrates.

The adhesive composition used in forming the absorbent composites of the present invention suitably does not detract from the elastic performance characteristics of the substrate or substrates to which the absorbent composite is secured by the adhesive composition in making the absorbent article. For example, as determined by an Elongation and Recovery Test set forth later herein, the absorbent article of the present invention suitably has a normalized load value at about 40 percent elongation thereof in at least one of the lateral direction and the longitudinal direction of the article of less than about 400 grams-force, and more suitably less than about 200 grams-force. At about 100 percent elongation, the absorbent article suitably has a normalized load value as determined by the Elongation and Recovery Test in at least one of the lateral direction and the longitudinal direction of the article of less than about 500 grams-force, and more suitably less than about 400 grams-force.

The absorbent article also suitably has a recovery as determined by the Elongation and Recovery Test in at least one of the longitudinal and lateral directions of the article, and more suitably both directions, that is at least about 60 percent of the recovery of the substrate(s) to which the absorbent composite is secured as determined by the Elongation and Recovery Test in the corresponding longitudinal and lateral directions of the article, more suitably at least about 80 percent, and even more suitably about 90 percent.

Figure 9:
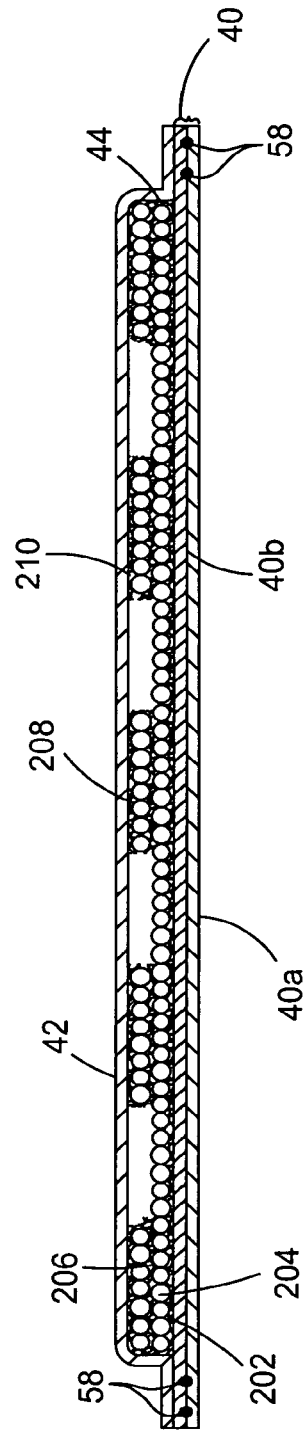
FIG. 9 is a schematic cross-section similar to that of FIG. 4 but of a fifth embodiment of an absorbent article of the present invention.

In an alternative embodiment illustrated in FIG. 9, the absorbent composite 44 is a multiple layer embodiment in which the basis weight of the absorbent composite is non-uniform across the width thereof. More particularly, the absorbent composite comprises a first layer 202 of adhesive composition applied to the inner layer 40b of the outer cover 40, and a first layer 204 of particulate superabsorbent material applied to and held by the first layer of adhesive composition. A second layer 206 of adhesive composition is applied to the first layer 204 of particulate superabsorbent material in a non-uniform pattern, so that portions of the particulate superabsorbent material are substantially free from being coated with the second layer of adhesive composition. As a result, a second layer 208 of particulate superabsorbent material applied to the non-uniform second layer 206 of adhesive composition is held in the absorbent composite according to the non-uniform pattern of the adhesive composition. A third layer 210 of adhesive composition is applied to the second layer 208 of superabsorbent material and the liner 42 is adhered to the absorbent composite 44 by the third layer of adhesive composition. However, the third layer of adhesive composition may be omitted and the liner may be free from securement to the absorbent composite 44 without departing from the scope of this invention.

It is contemplated that the basis weight of the absorbent composite 44 may be non-uniform across only a portion of the width thereof. It is also contemplated that the basis weight of the absorbent composite 44 may be non-uniform along all or a portion of the length of the absorbent composite.

Figure 10:
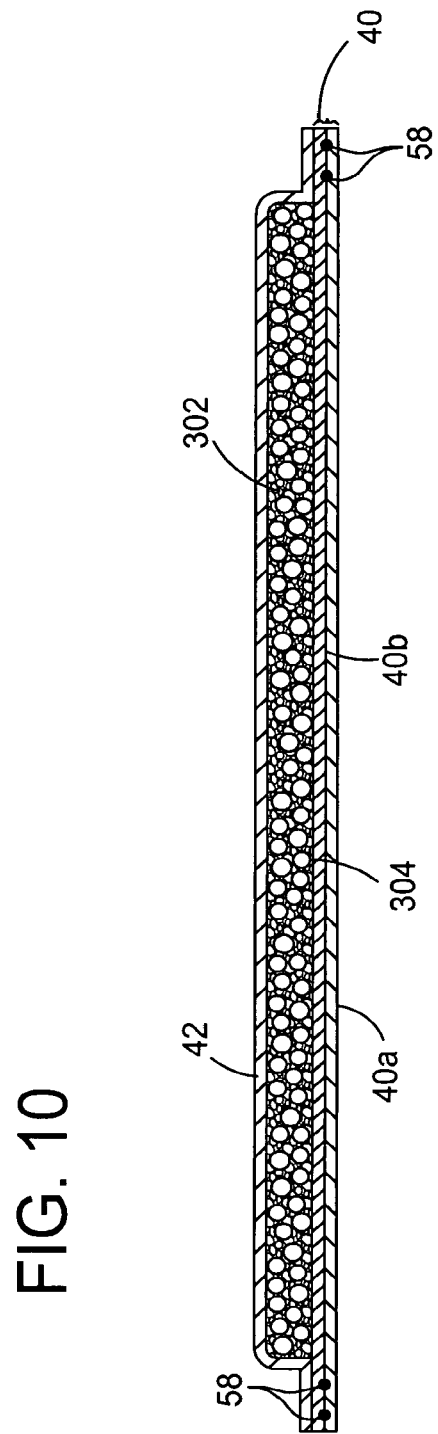
FIG. 10 is a schematic cross-section similar to that of FIG. 4 but of a sixth embodiment of an absorbent article of the present invention.

FIG. 10 illustrates another alternative embodiment in which the absorbent composite 44 comprises a blended or commingled mixture (e.g., instead of layering) of adhesive composition 302 and superabsorbent material 304. The adhesive composition 302 and superabsorbent material 304 may be any of the corresponding materials described previously herein. In a particularly suitable embodiment, a mixture of adhesive composition 302 and superabsorbent material 304 is formed and applied to the inner layer 40b of the outer cover 40 whereby the absorbent composite 44 is formed on the outer cover with the adhesive composition holding the superabsorbent material on the outer cover. As an example, in one embodiment particulate superabsorbent material may be fed into and entrained in a stream of adhesive composition, such as the adhesive composition stream shown in FIG. 6 and described previously herein, to form a blended mixture of adhesive composition and superabsorbent material that is applied to a moving substrate. The liner 42 overlays the absorbent composite 44 and is secured thereto by the adhesive composition 302. However, it is understood that the absorbent composite 44 need not be secured to the liner 42 to remain within the scope of this invention. It is also understood that the absorbent composite 44 may be applied to the liner 42 or other component of the pants 20 and remain within the scope of this invention.

In the illustrated embodiment of FIG. 10, the superabsorbent material 304 is uniformly distributed within the absorbent composite 44. However, it is contemplated that the superabsorbent material 304 may be distributed non-uniformly within the absorbent composite 44, e.g., to provided target areas of increased absorbency therein. It is also contemplated that in another embodiment the absorbent composite 44 may be a multi-layer composite in which one or more layers comprises individual layers of adhesive composition and/or superabsorbent material as shown in the embodiments of FIGS. 4, 5 and 7-9 and one or more layers of a mixture of adhesive composition and superabsorbent material as shown in the embodiment of FIG. 10.

Example 3

A continuous web was made comprising a pair of substrates, each constructed of a bicomponent (sheath/core, with 20 percent by weight polyethylene and 80 percent by weight KRATON elastomer) spunbond web having a basis weight of 1.0 ounces per square yard (osy) and treated with 1.0 percent by weight add on level of a mixture of surfactants (e.g., a 3 to 1 ratio of AHCOVEL surfactant and GLUCOPON surfactant). The web was formed at a speed of 9 feet/minute (2.74 meters/minute).

A meltblowing spray head, manufactured by J&M Laboratories, now Norsdon, of Norcross, Ga. as model AMBI-12-8 RMA 2132 was mounted on an adhesive applicator at a 45 degree angle to horizontal and at about 3 inches (7.62 cm) above the moving web. The head had 7 applicators, only five of which were used to form the absorbent composites. A hydrophilic adhesive, made by Bostik Findley of Milwaukee Wis. and designated HX 2773-01, was melted by a heater and then pumped to the spray head. The E1231-99 multicomponent superabsorbent particulate gel from BASF of Ludwigshafen, Germany was fed by a feeder (available from Christy Machine Company of Freemont, Ohio, as model COAT-O-MATIC 7"-D-S) into the stream of meltblown adhesive as the adhesive was sprayed from the spray head to achieve a blend of adhesive composition and superabsorbent material deposited onto one of the substrates. The other substrate was then laid over the absorbent composite in superposed relationship with the substrate on which the absorbent composite was formed.

The basis weight of the superabsorbent material was about 515 gsm and the basis weight of the adhesive composition was about 34 gsm. The total basis weight of the formed web, including the adhesive composite and substrates, was about 618 gsm. The width of each of the substrates was about 8.5 inches (21.6 cm) with the absorbent composite having a width of about 7 inches (17.8 cm) and centered laterally between the side edges of the substrates. The edges of the substrates were cut and removed so that the substrates were flush with the side edges of the absorbent composite, thereby forming the web to have a width of about 7 inches (17.8 cm).

The longitudinal direction of the web coincided with the machine direction of the substrates, e.g., the direction in which the substrates were moving during manufacture thereof. The lateral direction of the web coincided with the cross-machine direction of the substrates, e.g., the direction transverse to the machine direction thereof.

Experiment 3

An experiment was conducted to determine various elongation and recovery characteristics of samples cut from the webs formed in Example 1, Example 2 and Example 3 above and to compare these characteristics to the elongation and recovery characteristics associated with the respective substrates used in forming each of the webs of the Examples. Three-inch wide samples were cut from the webs formed in accordance with Examples 1, 2 and 3 and were subjected to the Elongation and Recovery Test set forth later herein to determine 1) the normalized load value (e.g., otherwise referred to herein as the tension) in the samples at 40 percent elongation thereof in each of the lateral direction and the longitudinal direction; 2) the normalized load value in the samples at 100 percent elongation thereof in each of the lateral direction and the longitudinal direction; 3) the set and recovery of the samples following elongation in each of the lateral direction and the longitudinal direction.

More particularly, a first set of 3-inch (7.6 cm) wide samples (each having a length of about 7 inches (17.8 cm)) was cut from the midline (e.g., on the longitudinal axis) of the web of Example 1 in the longitudinal (e.g., machine) direction and subjected to the Elongation and Recovery Test. A second set of three-inch wide (7.6 cm) samples (each having a length of about 7 inches (17.8 cm)) was cut from the web of Example 1 in the lateral (e.g., cross-machine) direction and subjected to the Elongation and Recovery Test. The results are provided in the table of FIG. 11. Similar sized samples were cut from the web of Example 2 and tested in the same manner. The results are provided in the table of FIG. 12. Similar sized samples were also cut from the web of Example 3 and tested accordingly, the results of which are provided in the table of FIG. 13.

For the samples cut laterally from the web of Example 1, the normalized load value at 40 percent elongation thereof (first cycle) was about 158 grams-force/inch. For samples cut in the longitudinal direction the normalized load value in the article at 40 percent elongation thereof as determined by the Elongation and Recovery Test was about 578 grams-force/inch. With respect to the articles formed in accordance with Example 2, the normalized load value at 40 percent elongation thereof (first cycle) in the laterally cut samples was about 216 grams-force/inch. In the longitudinal direction the normalized load value at 40 percent elongation was about 837 grams-force/inch. The normalized load values for the samples cut from the web of Example 3 were lower than those for Examples 1 and 2 in both the laterally and longitudinally cut samples.

For the laterally cut samples, the substrates used to form the web of Example 1 had a recovery (third cycle) of about 53.1 percent while the full samples of Example 1 had a recovery (third cycle) of about 50.9 percent, which is about 96 percent of the recovery of the substrates. The substrates used to form the web of Example 2 had a recovery of about 47.1 percent whereas the samples had a recovery of about 44.8 percent, which is about 95 percent of the recovery of the substrates. In the longitudinally cut samples, the recovery of the full samples cut from the web of Example 1 was approximately 98 percent of the recovery of the substrates of the web of Example 1 and the recovery of the full samples cut from the web of Example 2 was approximately 100 percent of the recovery of the substrates used in making the web of Example 2. The recovery of the full samples cut from the web of Example 3 was also about 100 percent for both the laterally cut and longitudinally cut samples.

Comparative Example 1

A continuous web was made substantially the same as the web of Example 3, but with each of the substrates from which the web was formed being replaced by a non-stretchable tissue material available from Cellu-Tissue of Neenah, Wis., U.S.A. This tissue material has a basis weight of about 18 gsm. The width of the web was formed to be about 7 inches (17.8 cm) in the same manner as the web of Example 3. The superabsorbent material had a basis weight of about 388 gsm and the adhesive composition had a total basis of about 25 gsm so that the total basis weight of the web (e.g., including the two layers of tissue material) was about 449 gsm. The web made in accordance with this comparative example did not support tensile elongation beyond about 5 percent without rupture.

Comparative Example 2

A continuous web was made substantially the same as the web of Example 3 but with the substrates being replaced by a releasable (e.g., non-stick) paper having one side coated with silicon. After the absorbent composite set up between the layers of releasable paper, the paper was removed from both sides of the absorbent composite. The superabsorbent material had a basis weight of about 388 gsm and the adhesive composition had a basis of about 25 gsm so that the total basis weight of the absorbent composite was about 413 gsm. The absorbent composite made in accordance with this comparative example did not support tensile elongation beyond about 5 percent without rupture.

The absorbent composite 44 in any of the various embodiments illustrated in FIGS. 4, 5 and 7-9 and described herein may further comprise hydrophilic fibers applied to the adhesive composition along with the particulate superabsorbent material. Examples of suitable hydrophilic fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

It is also understood that additional components or layers may be disposed between the liner 42 and the outer cover 40 generally in contact with the absorbent composite 44. For example, the pants 20 may further comprise a surge layer (not shown), which may also be broadly referred to as a substrate, disposed between the absorbent composite 44 and the bodyside liner 42. Surge layers are generally well known in the art as being constructed to quickly collect and temporarily hold liquid surges, and to transport the temporarily held liquid to the absorbent composite 44. Various woven and non-woven fabrics can be used to construct the surge layer. For example, the surge layer may be a layer made of a meltblown or spunbond web of synthetic fibers, such as polyolefin fibers. The surge layer may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The surge layer may be composed of a substantially hydrophobic material, and the hydrophobic material may optionally be treated with a surfactant or otherwise processed to impart a desired level of wettability and hydrophilicity.

Additional materials suitable for the surge layer are set forth in U.S. Pat. No. 5,486,166 issued Jan. 23, 1996 in the name of C. Ellis et al. and entitled "FIBROUS NONWOVEN WEB SURGE LAYER FOR PERSONAL CARE ABSORBENT ARTICLES AND THE LIKE"; U.S. Pat. No. 5,490,846 issued Feb. 13, 1996 in the name of Ellis et al. and entitled "IMPROVED SURGE MANAGEMENT FIBROUS NONWOVEN WEB FOR PERSONAL CARE ABSORBENT ARTICLES AND THE LIKE"; and U.S. Pat. No. 5,364,382 issued Nov. 15, 1994 in the name of Latimer et al. and entitled "ABSORBENT STRUCTURE HAVING IMPROVED FLUID SURGE MANAGEMENT AND PRODUCT INCORPORATING SAME", the disclosures of which are hereby incorporated by reference in a manner consistent with the present document.

The surge layer may be free from securement to the bodyside liner 42 and the absorbent composite 44, or it may be secured to one or both of the bodyside liner and the absorbent composite. It is also contemplated that the absorbent composite 44 may be formed on the surge layer instead of the liner 42 or outer cover 44, with the resulting laminate then being disposed between the liner and outer cover, without departing from the scope of this invention.

Alternatively, or additionally, a layer of perforated tissue (not shown) may be disposed between the liner 42 and the absorbent composite 44 to facilitate wicking and intake of liquid body exudates away from the liner.

In use, when the pants 20 of the present invention are subjected to various forces, such as those caused by initially fitting the pants on the wearer, by walking, sitting, twisting and like, and/or upon loading of the absorbent composite 44 (e.g., upon absorption of liquid body exudates), the stretchable outer cover 40 and/or liner 42 stretch to provide a more comfortable fit on the wearer. As the substrate (e.g., the outer cover 40 and/or liner 42) on which the absorbent composite 44 is formed or to which it is otherwise secured stretches, the superabsorbent material particles, which are secured to the substrate by the adhesive composition, move with the substrate such that adjacent particles are spaced from each other. Between adjacent superabsorbent material particles, adhesive composition bonds as well as adhesive composition to superabsorbent particle bonds tend to break down as the particles are spaced apart. However, the integrity of adhesive composition bonding the particles to the substrate (e.g., the outer cover 40 and/or liner 42) remains substantially intact so that upon relaxation of the substrate (e.g., movement toward the relaxed or unstretched configuration of the substrate), the particles move with the substrate back toward their initial position (e.g., as much as the recovery properties of the substrate will allow). Thus, the adhesive composition generally inhibits redistribution and accumulation of superabsorbent material particles away from a target area.

In some embodiments, the adhesive composition may retain sufficient tackiness such that upon relaxing of the substrate, the broken adhesive composition/adhesive composition bonds and/or the broken adhesive composition/superabsorbent material particle bonds between adjacent particles may reform as the particles are moved closer together.

Where the basis weight of the absorbent composite is non-uniform, such as in the embodiment illustrated in FIG. 9, the areas of lower basis weight are generally weaker than the areas of higher basis weight. As a result, the superabsorbent material particles in the areas of lower basis weight will tend to be pulled apart more so than in the areas of the higher basis weight. In this manner, superabsorbent particles within certain target areas of the absorbent composite, having areas of higher basis weight, are less prone to shifting.

Viscosity Test

The Viscosity Test is conducted in accordance with ASTM Test Method D3236-88, entitled "Standard Test Method for Apparent Viscosity of Hot Melt Adhesives and Coating Materials," the entire disclosure of which is incorporated herein by reference, with the following parameters. The viscometer used is that made by Brookfield Engineering Laboratories of Middleboro, Mass., U.S.A., as model RVDV III. The spindle number to use in conducting the ASTM Test Method is SC4-27. The sample size should be about 10.5 grams of adhesive. The spindle speed (rpm) is set to a value that results in a torque reading in the range of 20 percent to 80 percent. A reading should be taken every few minutes for about 15 minutes, or until the viscosity values stabilize, after which the final viscosity reading (in centipoises) is recorded.

Rheology Test

The Rheology Test as set forth herein is used to determine the storage modulus and glass transition temperature of a hot-melt adhesive. The Rheology Test is conducted generally in accordance with ASTM Test Method D4440-01, entitled "Standard Test Method for Plastics: Dynamic Mechanical Properties Melt Rheology," the entire disclosure of which is incorporated herein by reference to the extent that it is consistent herewith.

The Rheology Test is conducted using an Advanced Rheometric Expansion System (ARES) rheometer, available from TA Instruments of New Castle, Del., U.S.A. The ARES rheometer is equipped with a transducer, available from TA Instruments as model no. 2K FRTN1, and software which is also available from TA Instruments under the tradename ORCHESTRATOR, version 6.5.1. The ARES rheometer also uses 8 mm parallel plates, which are available from TA Instruments.

The 8 mm plates are installed in the ARES rheometer by first using the stage control buttons of the rheometer to raise the stage to thereby provide sufficient room for installing the plates. With motor on and in dynamic mode, the upper and lower plates are mounted on the actuator shafts of the rheometer. The torque and normal force are each zeroed by pressing the XDCR ZERO button on the user interface. The stage is then lowered to a point at which the plates are close but not touching. Using the ZERO FIXTURE button in the set gap/instrument control function under the Control menu of the software, the plates are brought together and the zero point determined for the plates. The stage is then raised to separate the plates a sufficient distance for loading a test sample therebetween.

The hot-melt adhesive sample to be tested should be larger than each 8 mm plate (e.g., as initially formed or otherwise cut from a larger sample), and should have a thickness of at least 2 mm. The adhesive sample is placed on the lower plate and the stage is lowered until a compressive force of approximately 50 to 100 grams is generated. The adhesive sample is then heated to its softening point. The gap reading on the user interface should be between 0.5 and 5 mm, and more suitably between 1 and 3 mm. If necessary, the stage can be raised or lowered to adjust the gap. Excess adhesive (e.g., exterior of the peripheral edges of the plates) is removed using a hot soldering iron.

The test conditions to be specified in the software are as follows:

The temperature control is set for that associated with using liquid nitrogen.
Geometry is set to 8 mm plates
Read Test Fixture Gap: "ON"
Testing Mode: Dynamic Temperature Ramp
Frequency: 6.28 radians/second
Ramp Rate: 3 degrees/minute
Initial Temperature: −20 degrees Celsius
Final Temperature: 100 degrees Celsius
Strain: 0.5 percent
Time per measure: 5 seconds
Auto Tension Adjustment: "ON"
Initial Static Force: 300 grams
Auto Tension Sensitivity: 300 grams In the ORCHESTRATOR software, under the Control menu, select EDIT/START TEST and then select BEGIN TEST to start the test. Once the sample has been tested, the software is used to plot the storage modulus (G'), in dynes/square centimeter, on the primary y-axis; tan delta on the secondary y-axis, and temperature, in degrees Celsius, on the X-axis. The storage modulus (G') at 25 degrees Celsius for the adhesive sample is determined from the plot. The glass transition temperature (Tg) is the temperature (on the plot) at which the maximum peak occurs on the tan delta versus temperature curve.

Elongation and Recovery Test

The Elongation and Recovery Test is a three cycle elongation and recovery test used to measure the elongation and recovery characteristics of an absorbent article, and more particularly of a test specimen comprising an absorbent composite secured to one or more substrates or other components. In particular, the Test may be used to determine what affect, if any, securing the absorbent composite to the substrate(s) has on the elongation and recovery characteristics thereof. The Test measures load values of a test sample placed under a particular amount of strain (e.g., elongated to a particular elongation). Such load values are determined during both the elongation and recovery phases of the Test, and during each of the three cycles. The recovery of each test sample is determined by the degree of permanent elongation after the load value drops to 3.3 grams-force (gf) per inch of sample width during the recovery phase. The Test is conducted on the specimen (e.g., the absorbent composite secured to the substrate(s)) as well as on the substrate(s) independent of the absorbent composite and the results are compared.

Sample Preparation

Six samples of the test specimen should be subjected to the Elongation and Recovery Test, three samples of the full specimen and three samples of the substrate(s) independent of (e.g., separated from) the absorbent composite of the specimen, and the results for each set of three samples should be averaged. Each sample should be approximately 3 inches (76 mm) wide by at least 5 inches (127 mm) long, and more preferably at least 6 inches (152 mm) long. Where the specimen is taken from a manufactured article having a width greater than 3 inches, the samples should be cut from the midline of the specimen, i.e., samples which include the widthwise edges of the article should be avoided to reduce the risk that edge effects may cause inconsistent results in testing.

The sample should be free from attachment to any other article components that may be present, such as leg or waist elastic structures, impermeable outer covers or liners (if not manufactured to be secured to the absorbent composite), etc., at least in the region to be used as a sample. Unrelated components can be present at the longitudinal ends of the sample (e.g., at the ends which are to be held within grips of the tester, as described later herein) only under the following circumstances: 1) they do not add substantially to the thickness of the sample and do not cause the effective gage length to increase (i.e., a sample end inside a grip is placed under tension because of irregular thickness of the sample), and 2) they do not affect the appearance or behavior of the region of the sample being tested (e.g., causing the sample to be rippled or contracted, or inhibiting the elongation of any part of the sample to be tested).

Where a given test specimen will not permit samples of the desired dimensions (e.g., 3 inches wide by at least 5 inches long) to be prepared, the length of the sample selected should be as long as possible while allowing sufficient material at the ends of the sample (e.g., at least ½ inch (13 mm) for gripping in the tensile tester). All samples of a given specimen must be tested at the same length. Samples having a length of one inch or less or a width of one inch or less should not be used.

Where the samples are to be taken from an already manufactured article, the substrate(s) to which the absorbent composite is secured must be separated from the absorbent composite for testing. This may be achieved by one of the following methods. Care should be taken to avoid stretching the substrate(s) during separation. The article (e.g., substrate(s) and absorbent composite secured thereto) from which the substrate(s) is/are to be taken should be cut to the desired sample dimensions prior to conducting one of the following to separate the substrate(s) from the absorbent composite.

1) The article may be frozen, such as with liquid nitrogen, to permit the substrate(s) to be separated from the absorbent composite; or 2) Depending on adhesive chemistry, the article may be treated with a solvent selected to dissolve the adhesive composition of the absorbent composite without affecting the structure or properties of the substrate(s).

Where an absorbent composite of the specimen to be tested is secured to more than one substrate or other components used to support or enclose the absorbent composite (e.g., one to each major face of the absorbent composite), the substrates or other components should be smoothly and gently overlaid with each other (in the same relative orientation as in the article) in flush alignment therewith, without elongating any of the substrates or other components, and tested together as a single sample.

Test Apparatus and Materials

The following test apparatus and materials are used to conduct the Elongation and Recovery Test.

1) Constant Rate of Extension (CRE) tensile tester: MTS tensile tester model SYNERGIE 200 TEST BED, available from MTS Systems Corporation, Research Triangle Park, N.C., USA.

2) Load cells: A suitable cell selected so that the majority of the peak load values fall between the manufacturer's recommended ranges of the load cell's full scale value. Load cell Model 100N available from MTS Systems Corporation is preferred.

3) Operating software and data acquisition system: MTS TESTWORKS for Windows software version 4, available from MTS® Systems Corporation.

4) Grips: pneumatic-action grips, top and bottom, identified as part number 2712-003 available from Instron Corporation, Canton, Mass. USA.

5) Grip faces: 25 mm by 100 mm.

Test Conditions

Reasonable ambient conditions should be used for sample testing, such as 73+/−2 degrees Fahrenheit (about 23 degrees Celsius) and a relative humidity of 50+/−2 percent. If the samples are stored under substantially different conditions, the samples should be measured after they equilibrate to laboratory conditions.

The instruments used should be calibrated as described in the manufacturer's instructions for each instrument.

The tensile tester conditions are as follows:
Break sensitivity: 60%
Break threshold: 200 grams-force
Data acquisition rate: 100 Hz
Preload?: No
Slowdown extension: 0 mm
Test speed: 508 mm/min.
Full scale load: 10,000 grams-force
Gage length: 4 inches (102 mm)
Number of cycles: 3

Test Procedure

Calibrate the load cell using the TESTWORKS software at the beginning of each work session. Using the tensile frame pushbutton controls for cross-head position, move the grips to provide a gage length (distance between grips) of 4 inches (102 mm). Calibrate the software to this initial gage length. Place the sample to be tested lengthwise so that it is centered between the grips, held in a centered position within each grip, and oriented correctly (e.g., with the widthwise dimension running transverse to the length between the grips), e.g., with the vertical (e.g., side) edges of the sample perpendicular to the grip faces. Close the grips on the sample, holding the sample in such a way as to minimize slack in the sample without placing the sample under tension.

Ensure that the load at this point is less than ±3.3 grams per inch of sample width. If the load is greater than 3.3 grams per inch width, release the lower grip and zero the load cell. Re-close the lower grip, again ensuring that the sample is neither under tension nor buckled with excessive slack. Continue checking the starting load and following the above procedure until the starting load is within the desired range.

Run the three cycle test using the above parameters by clicking on the RUN button. When the test is complete, save the data to a sample file. Remove the sample from the grips. Run the above procedures for the remaining samples of a given specimen. The data for all samples should be saved to a single file.

Report the data for each sample as follows: Average peak load @ 20, 40, 60, 80 and 100% elongation; Average percent set following each cycle; and Average percent recovery following each cycle. A specimen with a peak load that exceeds the limits of the load cell (~10,000 grams-force) should have a peak load listed as >10,000 grams-force. The average calculation for that sample should use 10,000 grams-force as the peak load for that specimen, with a notation made that the average is conservative (low) due to rounding down at least one peak load level to 10,000 grams-force.

The peak load should be normalized by dividing by the width of the sample to determine a normalized peak load per one inch of sample width. The normalized peak load of the specimen is considered to be the average normalized peak load during the first elongation cycle. Percent set and recovery values should be determined by recording the gage length (distance between grip faces) at which the load value on the recovery phase of each cycle drops to 3.3 grams-force per inch of sample width. For samples 3 inches in width, this is a load value of 10 grams-force.

The percent set of each sample is calculated by the following formula:

$$\frac{\text{gage length when load value of 3.3 grams-force per inch of sample width is reached on the last recovery cycle} - \text{starting length}}{\text{starting gage length}} \times 100$$

The percent recovery of each sample is calculated by the following formula: 100−percent set.

The above Test procedures are conducted first for all of the samples of the full specimen (absorbent composite secured to the substrate(s)), and again for all of the samples of the substrate(s) independent of the absorbent composite of the specimen. The effect of securing the absorbent composite to the substrate(s) is determined as follows:

(percent recovery of the full specimen divided by the percent recovery of the substrate(s))×100.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An absorbent composite for an absorbent article, the absorbent composite comprising:
   an adhesive composition and particulate superabsorbent material held by the adhesive composition, said adhesive composition having a viscosity of less than about 10,000 centipoises at a temperature of less than or equal to about 400 degrees Fahrenheit (about 204 degrees Celsius) and a storage modulus (G') of less than or equal to about $1.0 \times 10^7$ dyne/cm$^2$ at 25 degrees Celsius, the adhesive composition having a glass transition temperature (Tg) in the range of about −25 degrees Celsius to about 25 degrees Celsius.

2. An absorbent composite as set forth in claim 1 in combination with a stretchable substrate, the absorbent composite being secured to the substrate by the adhesive composition.

3. A combination as set forth in claim 2 further comprising a second substrate in generally superposed relationship with the stretchable substrate whereby the absorbent composite is disposed between said stretchable substrate and said second substrate.

4. A combination comprising:
   an absorbent composite comprising:
      an adhesive composition and particulate superabsorbent material held by the adhesive composition, said adhesive composition having a viscosity of less than about 10,000 centipoises at a temperature of less than or equal to about 400 degrees Fahrenheit (about 204 degrees Celsius) and a storage modulus (G') of less than or equal to about $1.0 \times 10^7$ dyne/cm$^2$ at 25 degrees Celsius; and
   a stretchable substrate, the absorbent composite being secured to the substrate by the adhesive composition, wherein the absorbent composite is formed on the stretchable substrate.

5. An absorbent composite as set forth in claim 1 wherein the absorbent composite comprises a layer of adhesive composition and a layer of particulate superabsorbent material applied to and held by the adhesive composition.

6. An absorbent composite as set forth in claim 5 in combination with a stretchable substrate, the layer of adhesive composition being applied to the stretchable substrate to secure the absorbent composite thereto and the layer of particulate superabsorbent material being applied to and held by the adhesive composition.

7. A combination as set forth in claim 3 wherein the second substrate is secured to the absorbent composite by the adhesive composition.

8. A combination as set forth in claim 7 wherein the absorbent composite comprises a first layer of adhesive composition, a first layer of particulate superabsorbent material applied to and held by the first layer of adhesive composition, and a second layer of adhesive composition applied to the first layer of particulate superabsorbent material, the stretchable substrate being secured to the absorbent composite by the first layer of adhesive composition and the second substrate being secured to the absorbent composite by the second layer of adhesive composition.

9. An absorbent composite as set forth in claim 1 wherein the adhesive composition comprises a hot-melt adhesive.

10. An absorbent composite as set forth in claim 1 wherein the adhesive composition has a viscosity of less than about 10,000 centipoises at a temperature of less than or equal to about 300 degrees Fahrenheit (about 149 degrees Celsius).

11. An absorbent composite as set forth in claim 10 wherein the adhesive composition has a viscosity of less than about 10,000 centipoises at a temperature of less than or equal to about 250 degrees Fahrenheit (about 121 degrees Celsius).

12. An absorbent composite as set forth in claim 1 wherein the adhesive composition has a viscosity in the range of about 1,000 to about 8,000 centipoises at a temperature of about 300 degrees Fahrenheit (about 149 degrees Celsius).

13. An absorbent composite as set forth in claim 12 wherein the adhesive composition has a viscosity in the range of about 2,000 to about 6,000 centipoises at a temperature of about 300 degrees Fahrenheit (about 149 degrees Celsius).

14. An absorbent composite as set forth in claim 1 wherein the adhesive composition has a storage modulus (G') in the range of about $1.0\times10^5$ to about $1.0\times10^6$ dyne/cm$^2$ at 25 degrees Celsius.

15. An absorbent composite as set forth in claim 1 wherein the adhesive composition has a glass transition temperature (Tg) in the range of about −10 degrees Celsius to about 25 degrees Celsius.

16. An absorbent composite as set forth in claim 1 further comprising hydrophilic fibers.

17. An absorbent composite as set forth in claim 1 wherein the absorbent composite has a width and a length, said absorbent composite having a non-uniform basis weight across at least a portion of at least one of the width and the length of said absorbent composite.

18. A combination as set forth in claim 2 wherein the substrate defines an outer cover of an absorbent article, the absorbent article further comprising a liquid permeable liner in generally superposed relationship with the outer cover and adapted for contiguous relationship with the wearer's skin, the absorbent composite being disposed between the liner and the outer cover.

19. An absorbent composite as set forth in claim 5 wherein the layer of adhesive composition is a first layer of adhesive composition and the layer of particulate superabsorbent material is a first layer of particulate superabsorbent material, the absorbent composite further comprising a second layer of adhesive composition applied to the first layer of particulate superabsorbent material, and a second layer of particulate superabsorbent material applied to and held by the second layer of adhesive composition.

20. An absorbent composite as set forth in claim 1 wherein the absorbent composite comprises a mixture of adhesive composition and superabsorbent material.

21. An absorbent composite for an absorbent article, the absorbent composite comprising:
an adhesive composition and particulate superabsorbent material held by the adhesive composition, said adhesive composition having a viscosity of less than about 10,000 centipoises at a temperature of less than or equal to about 400 degrees Fahrenheit (about 204 degrees Celsius) and a storage modulus (G') of less than or equal to about $1.0\times10^7$ dyne/cm$^2$ at 25 degrees Celsius, wherein the adhesive composition is hydrophilic.

22. An absorbent composite as set forth in claim 1 wherein the adhesive composition is hydrophobic.

23. A combination comprising:
an absorbent composite comprising:
an adhesive composition and particulate superabsorbent material held by the adhesive composition, said adhesive composition having a viscosity of less than about 10,000 centipoises at a temperature of less than or equal to about 400 degrees Fahrenheit (about 204 degrees Celsius) and a storage modulus (G') of less than or equal to about $1.0\times10^7$ dyne/cm$^2$ at 25 degrees Celsius; and
a substrate, the absorbent composite being secured to the substrate by the adhesive composition, wherein the absorbent composite is formed on the substrate.

\* \* \* \* \*